United States Patent
Baek et al.

(10) Patent No.: US 11,008,333 B2
(45) Date of Patent: May 18, 2021

(54) CRYSTALLINE FORMS OF HYDROCHLORIDE SALTS OF THIENOPYRIMIDINE COMPOUND

(71) Applicant: HANMI PHARM. CO., LTD., Hwaseong-si (KR)

(72) Inventors: Jong Ouk Baek, Hwaseong-si (KR); Ji Young Jeon, Hwaseong-si (KR); Hee Sook Oh, Hwaseong-si (KR); Hee Cheol Kim, Hwaseong-si (KR); Sun Young Jang, Hwaseong-si (KR); Tae Hee Ha, Hwaseong-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 366 days.

(21) Appl. No.: 16/066,388

(22) PCT Filed: Dec. 30, 2016

(86) PCT No.: PCT/KR2016/015535
§ 371 (c)(1),
(2) Date: Jun. 27, 2018

(87) PCT Pub. No.: WO2017/116192
PCT Pub. Date: Jul. 6, 2017

(65) Prior Publication Data
US 2020/0270268 A1    Aug. 27, 2020

(30) Foreign Application Priority Data

Dec. 31, 2015 (KR) .................. 10-2015-0190853
May 27, 2016 (KR) .................. 10-2016-0065977

(51) Int. Cl.
*C07D 495/04* (2006.01)
*A61P 35/00* (2006.01)

(52) U.S. Cl.
CPC ........ *C07D 495/04* (2013.01); *C07B 2200/13* (2013.01)

(58) Field of Classification Search
CPC .................... C07B 2200/13; C07D 495/04
See application file for complete search history.

(56) References Cited

U.S. PATENT DOCUMENTS

| | | | |
|---|---|---|---|
| 6,245,759 B1 | 6/2001 | Bilodeau et al. | |
| 7,781,433 B2 | 8/2010 | Chuckowree et al. | |
| 2012/0065233 A1 | 3/2012 | Gregor et al. | |
| 2013/0116213 A1* | 5/2013 | Cha ..................... | A61P 7/04 514/81 |

FOREIGN PATENT DOCUMENTS

| | | |
|---|---|---|
| KR | 10-2014-0118575 A | 10/2014 |
| RU | 2008 145 663 A | 6/2010 |
| WO | 2011/162515 A2 | 12/2011 |
| WO | 2015112705 A2 | 7/2015 |
| WO | 2015134242 A1 | 9/2015 |
| WO | 2016/201370 A1 | 12/2016 |
| WO | 2017116193 A1 | 7/2017 |

OTHER PUBLICATIONS

Bhattacharya et al. (Brittain, ed. Polymorphism in Pharmaceutical Solids, 2009, p. 334.*
Wiedmann et al. (Asian Journal of Pharmaceutical Sciences, 2016, 11 (6), pp. 722-734).*
Berge et al., "Pharmaceutical Salts", Journal of Pharmaceutical Sciences, Jan. 1977, vol. 66, No. 1, pp. 1-19 (total 19 pages).
Morissette et al., "High-throughput crystallization: polymorphs, salts, co-crystals and solvates of pharmaceutical solids", Advanced Drug Delivery Reviews, 56 (2004), pp. 275-300 (total 26 pages).
Caira, "Crystalline Polymorphism of Organic Compounds", Topics in Current Chemistry, 1998, vol. 198, pp. 163-208 (total 46 pages).
Moskva, "Solvents in Oranic Chemist," 1999, No. 4, pp. 44-50 (total 7 pages).
Manisha S. Phoujdar, et al., "Microwave-based synthesis of novel thienopyrimidine bioisosteres of gefitinib", Tetrahedron Letters, 2008, pp. 1269-1273, vol. 49.
Chemical Abstract compunds, STN express, RN1938072-69-5, entered STN: Jun. 23, 2016, RN1842366-97-5, entered STN: Jan. 7, 2016, 2 pages.
International Searching Authority, International Search Report for PCT/KR2016/015535 dated Mar. 31, 2017 [PCT/ISA/210].

* cited by examiner

*Primary Examiner* — Susanna Moore
(74) *Attorney, Agent, or Firm* — Sughrue Mion, PLLC

(57) ABSTRACT

A crystalline form of an alkyl benzene sulfonyl urea compound that is useful as an oral antidiabetics is disclosed. Specifically, the compound is a hydrochloride salt of N-(3-(2-(4-(4-methylpiperazin-1-yl)phenylamino)thieno[3,2-d]pyrimidin-4-yloxy)phenyl)acrylamide of the following formula I. A pharmaceutical composition containing the compound is also disclosed:

Formula I

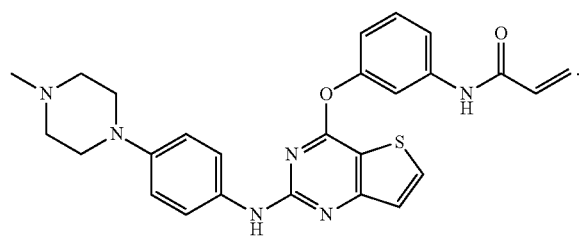

26 Claims, 23 Drawing Sheets

【Figure 1A】
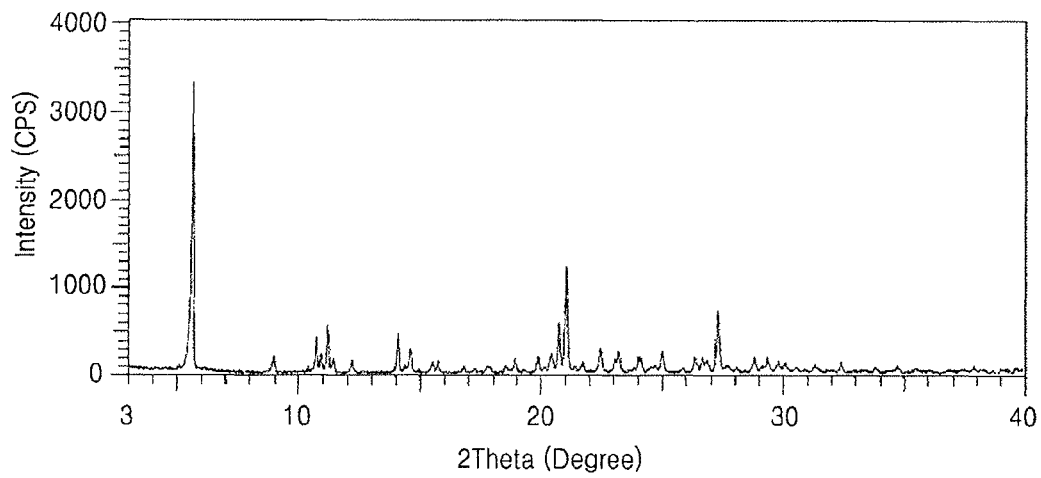
【Figure 1B】
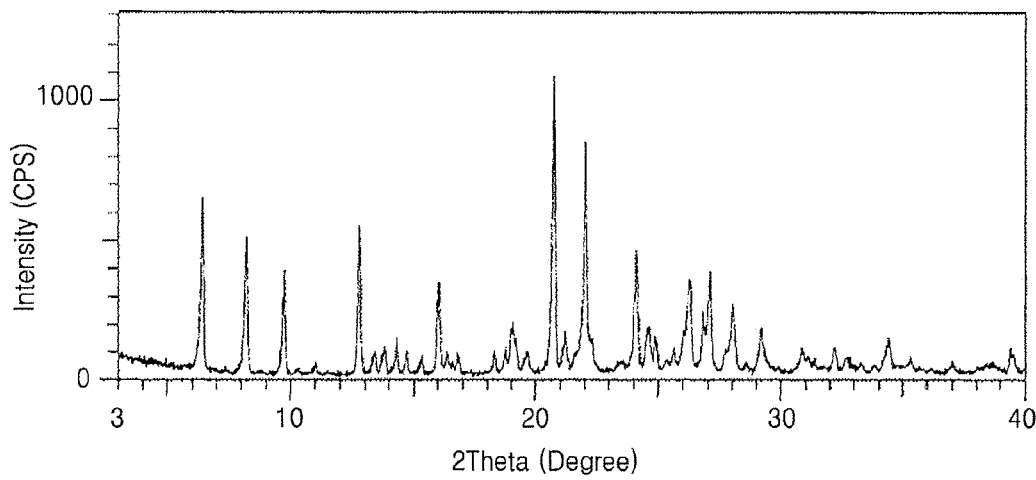

[Figure 1C]
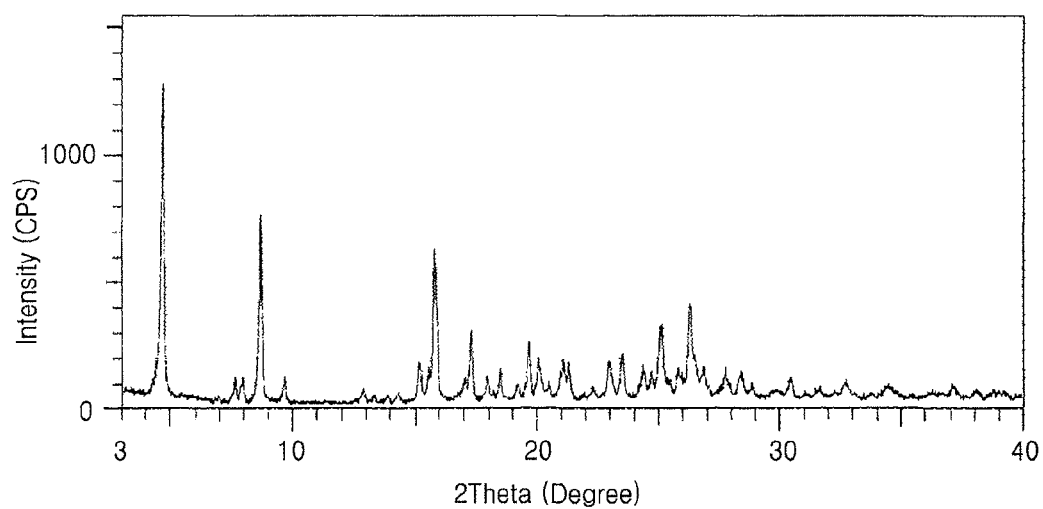
[Figure 1D]
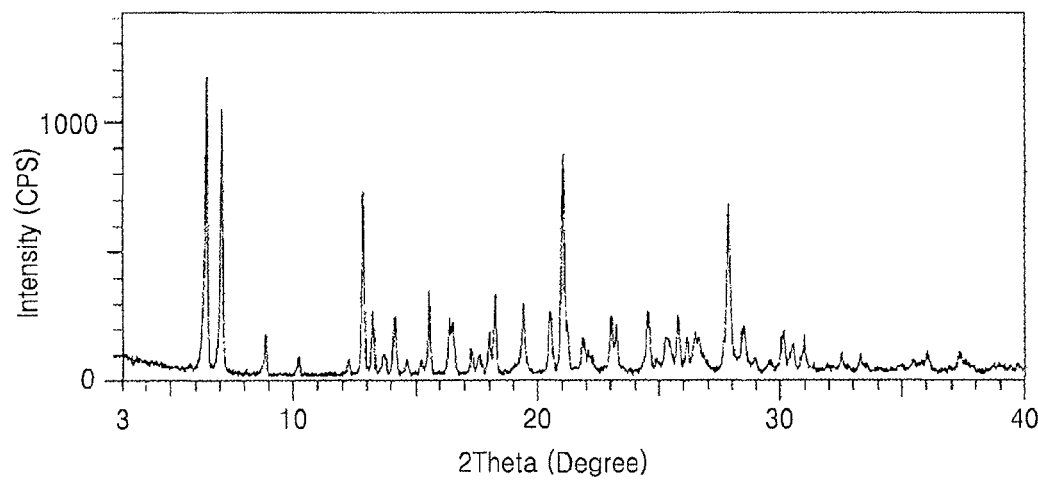

【Figure 1E】
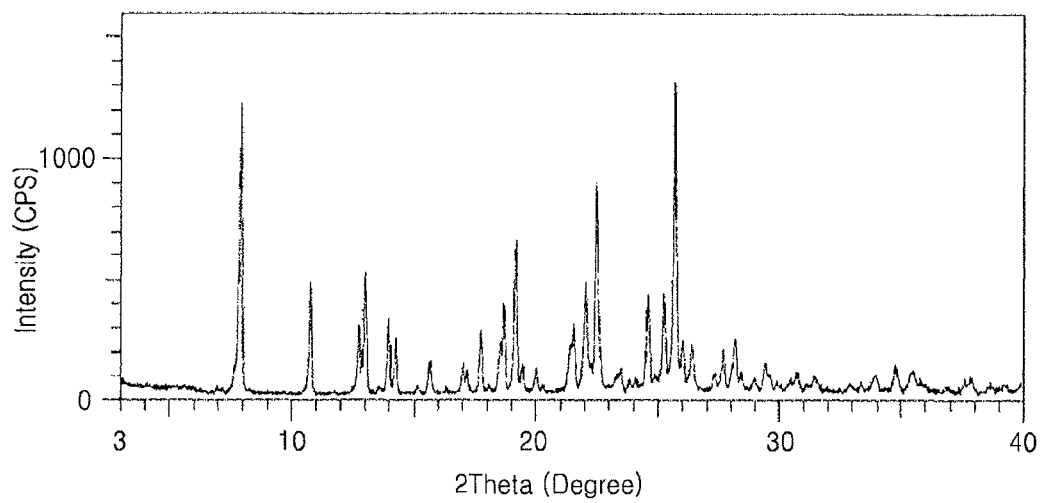
【Figure 1F】
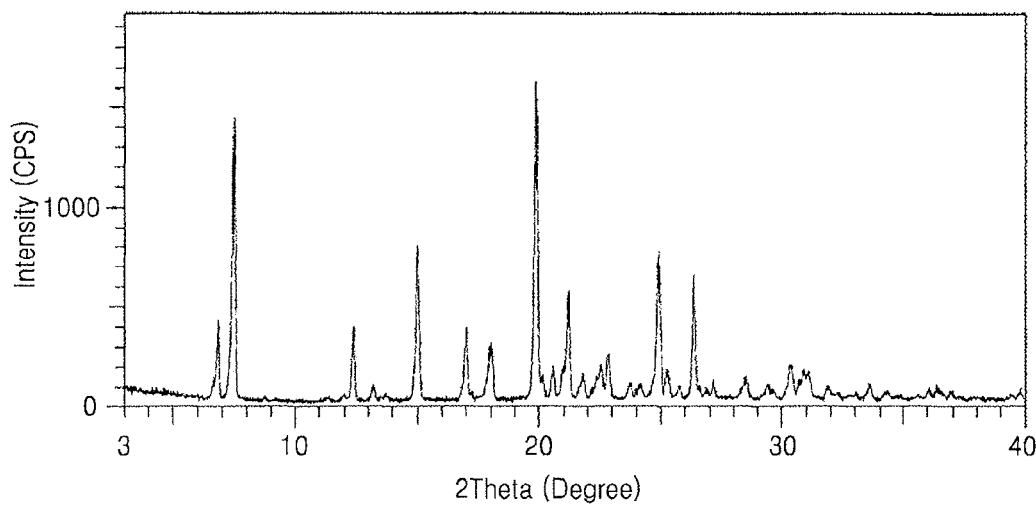

【Figure 1G】
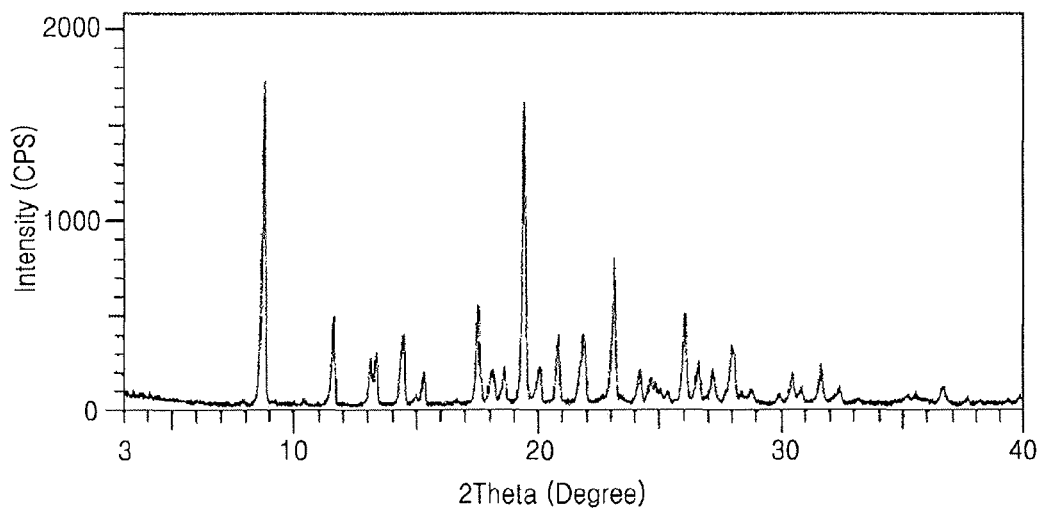
【Figure 1H】
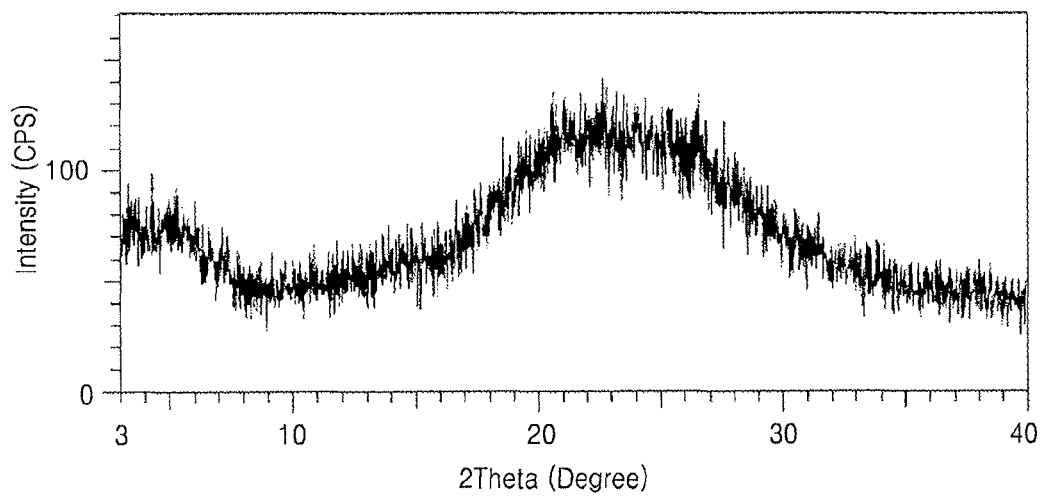

[Figure 2A]
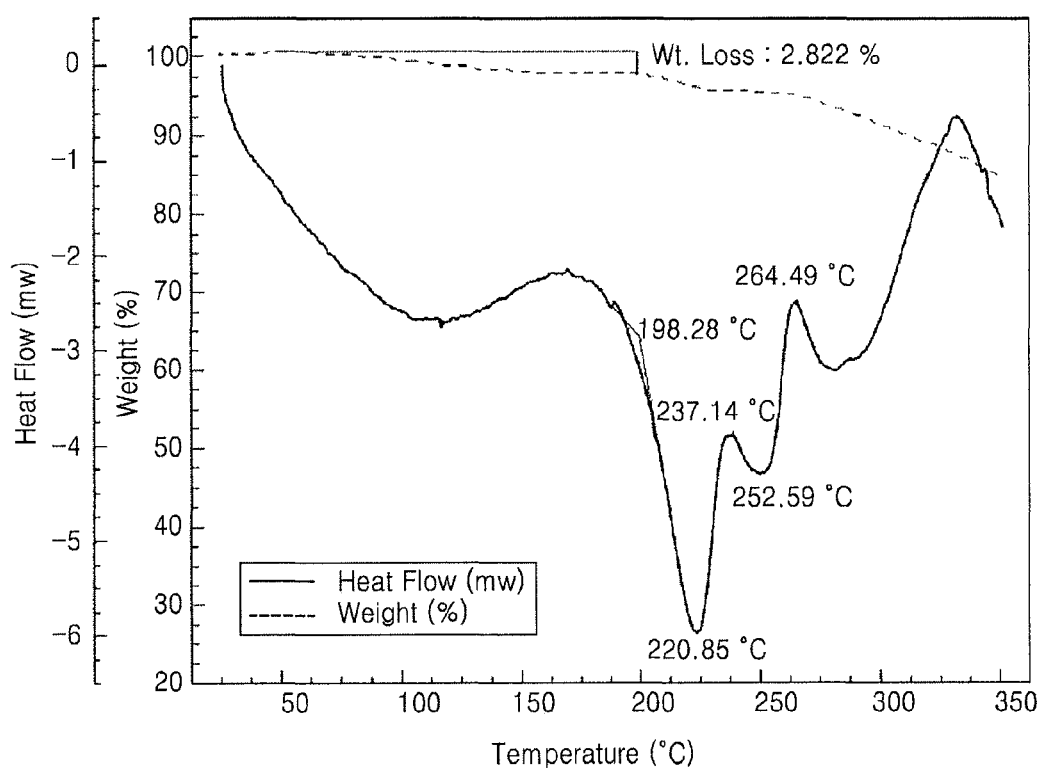

[Figure 2B]
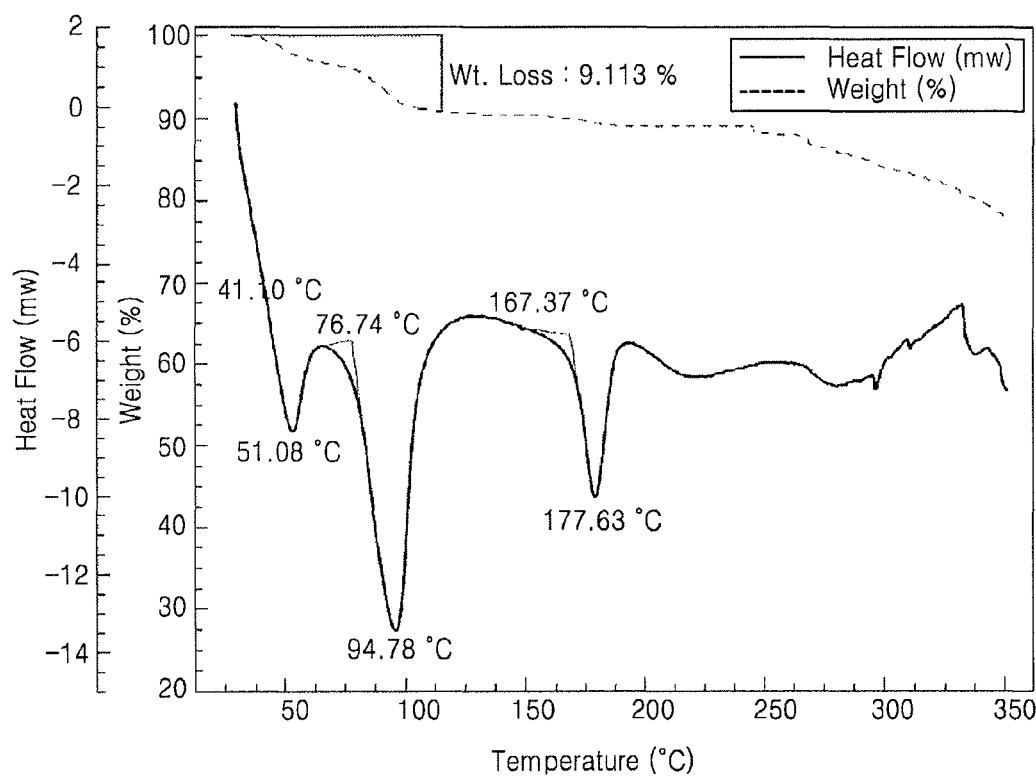

[Figure 2C]
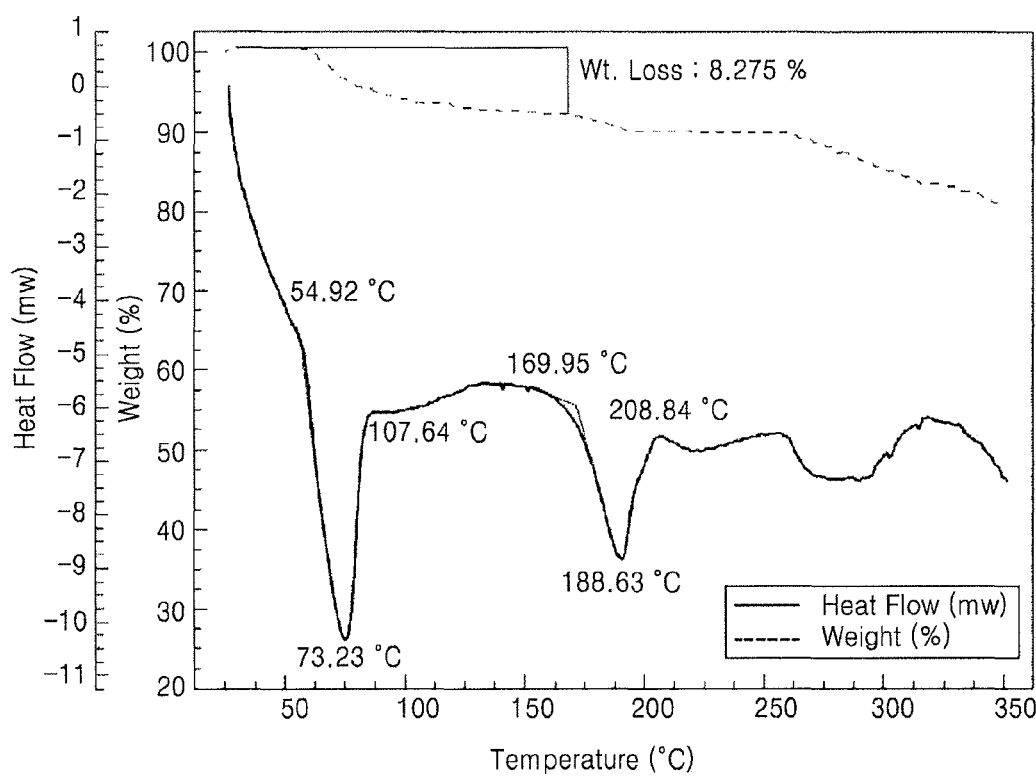

[Figure 2D]
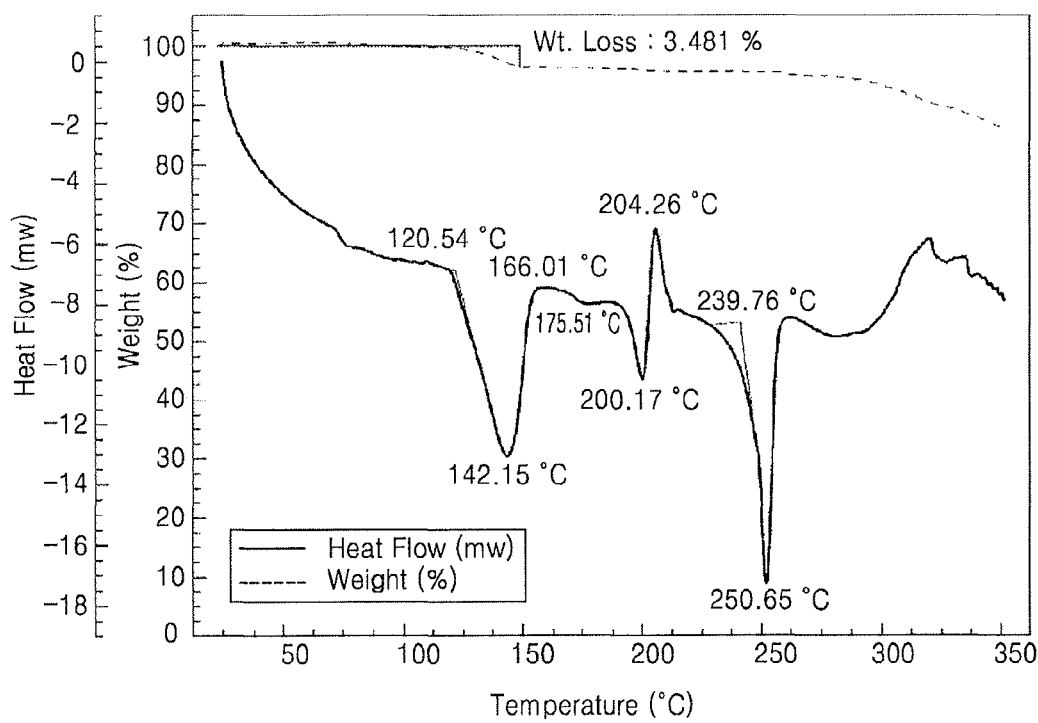

[Figure 2E]
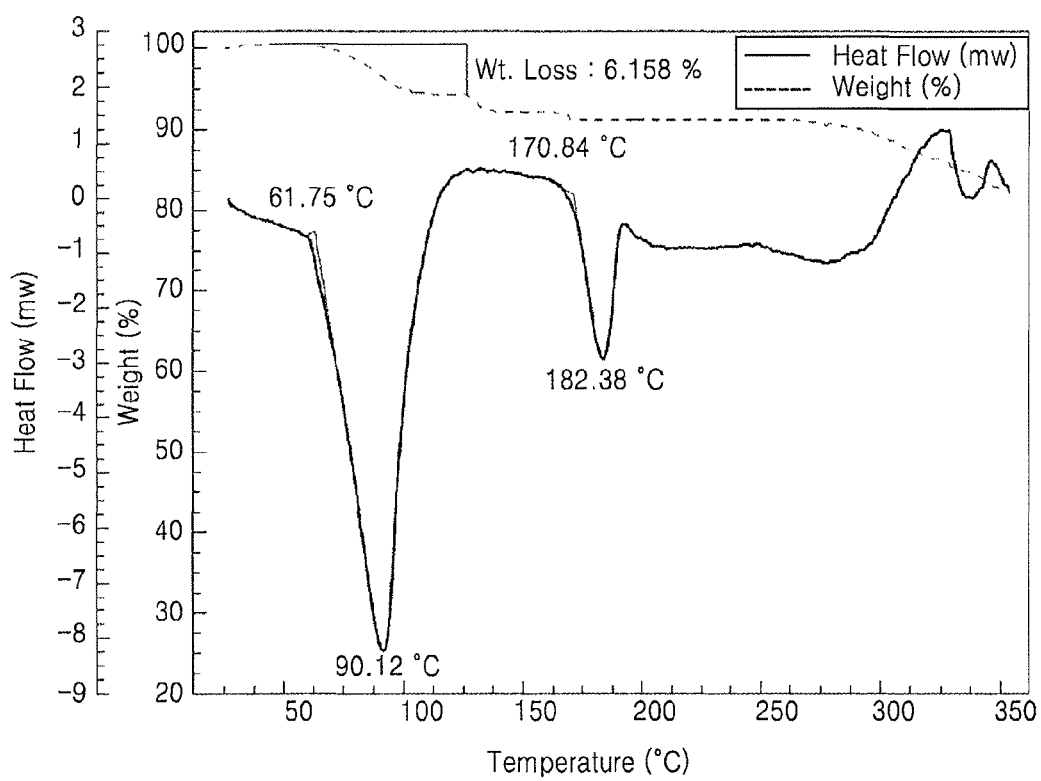

[Figure 2F]
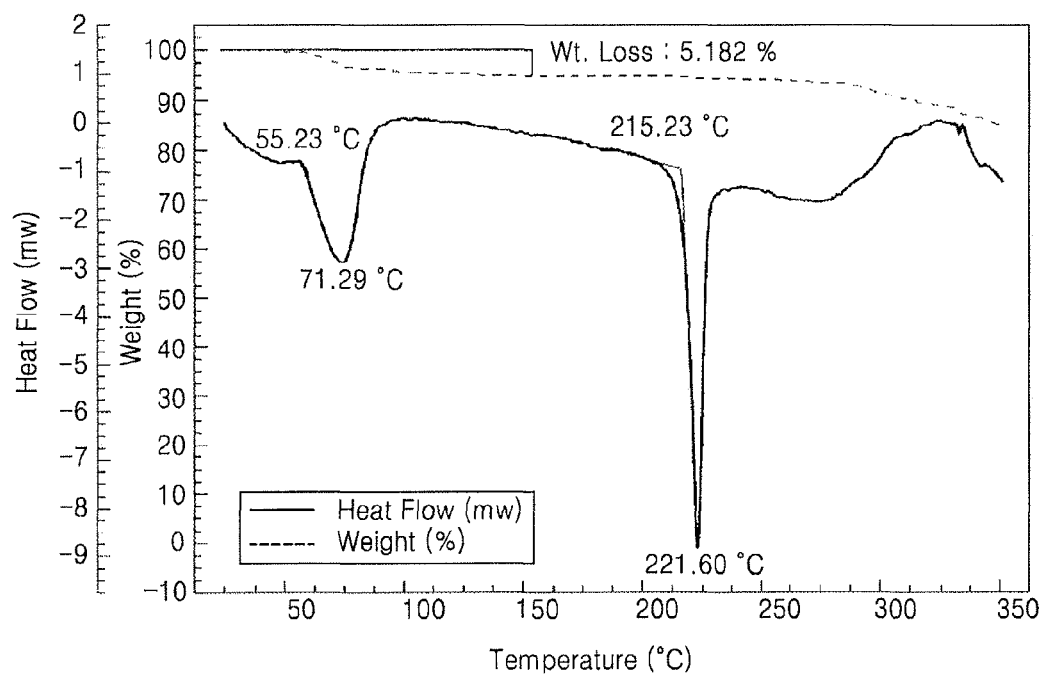

[Figure 2G]
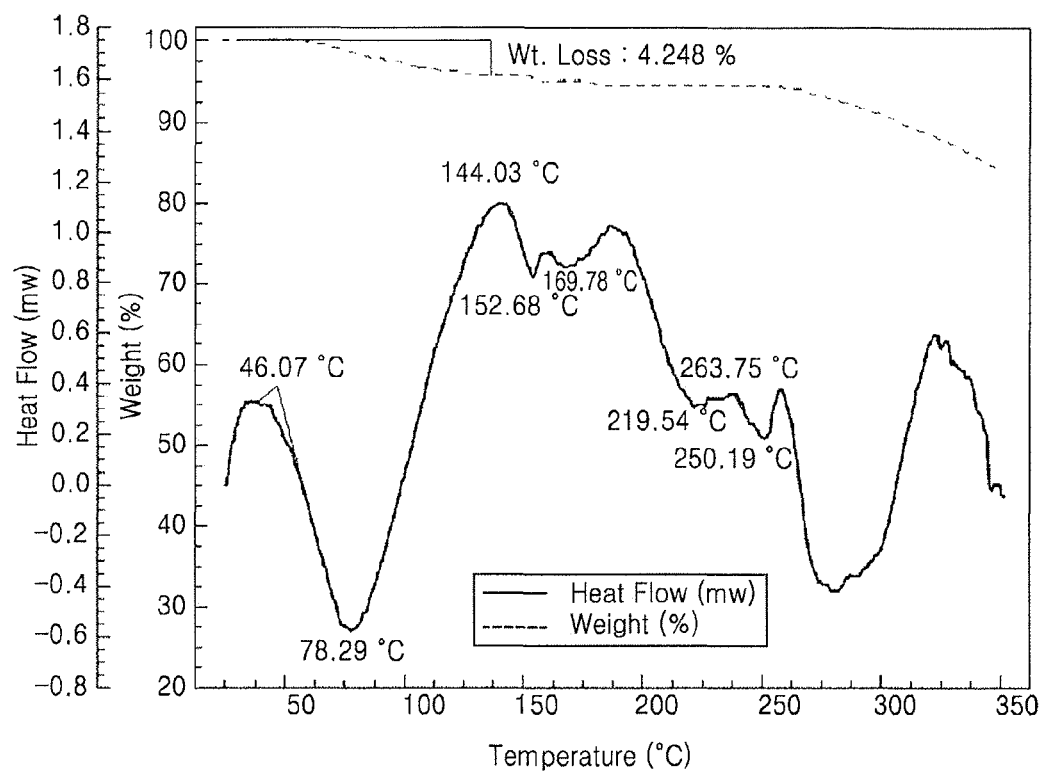

[Figure 3A]
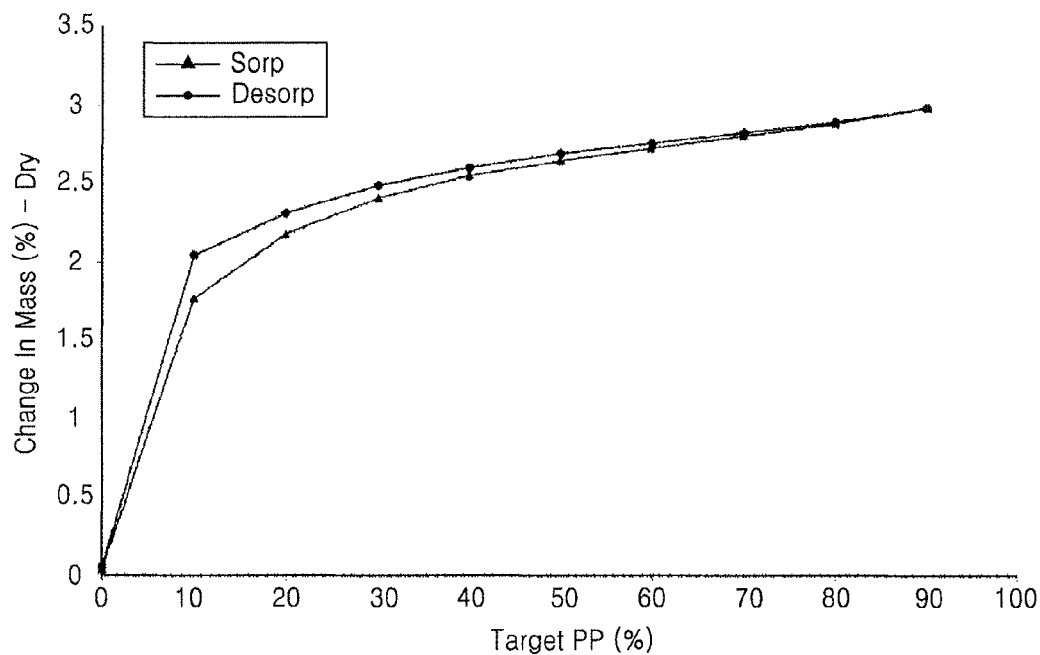
[Figure 3B]
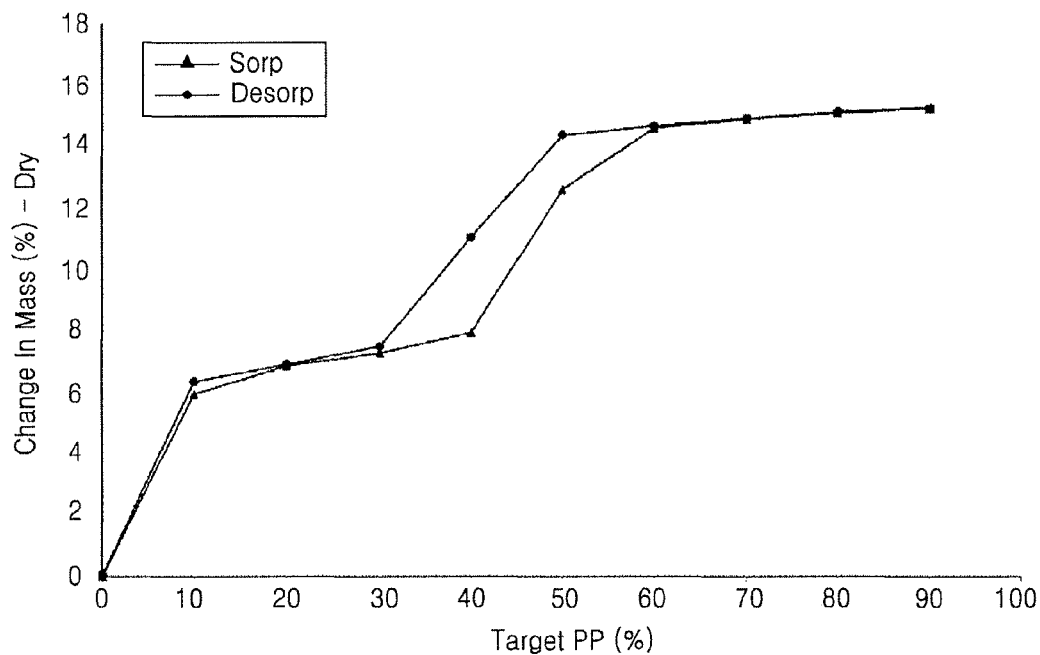

[Figure 3C]
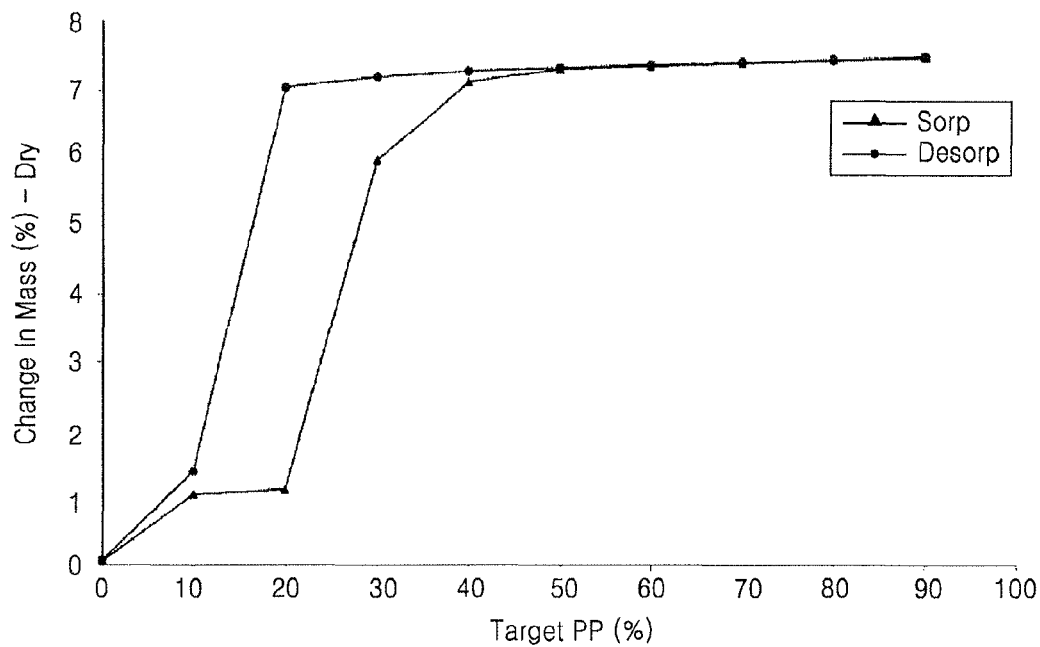
[Figure 3D]
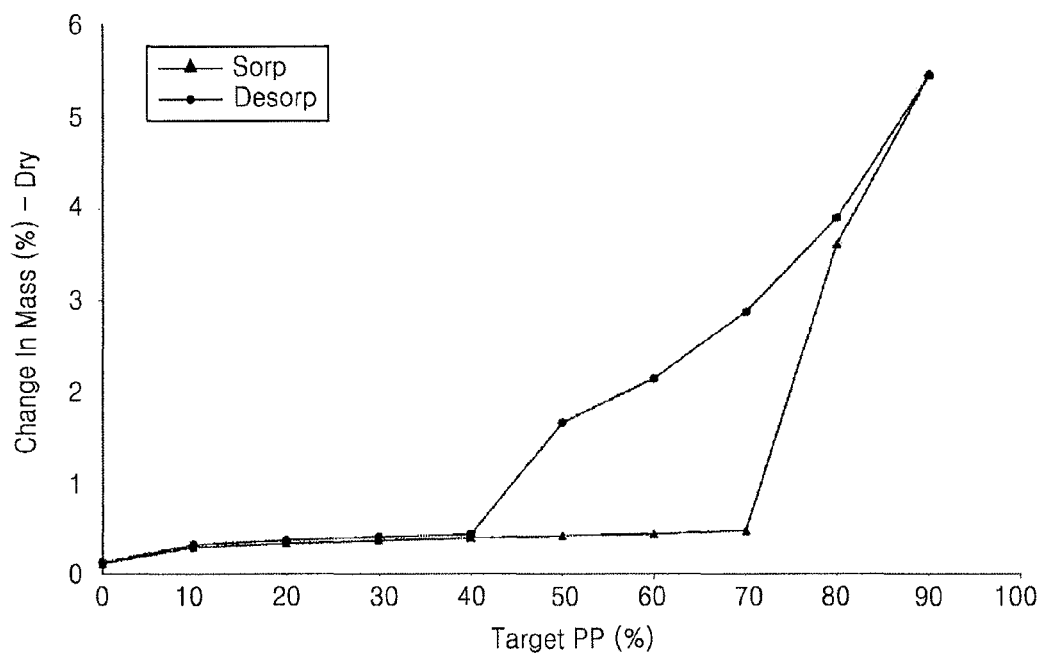

[Figure 3E]
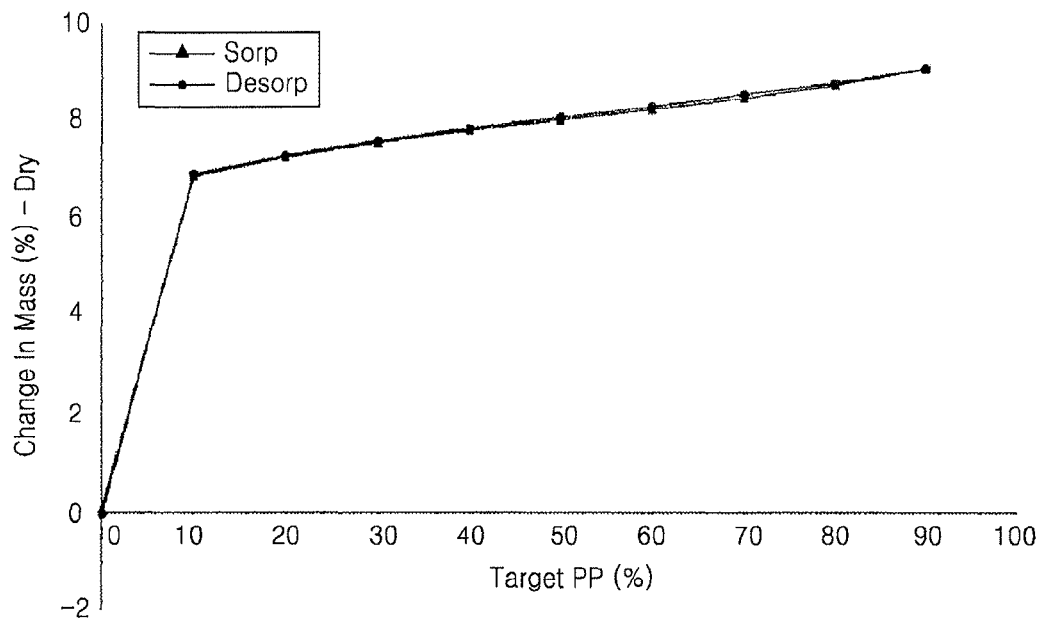
[Figure 3F]
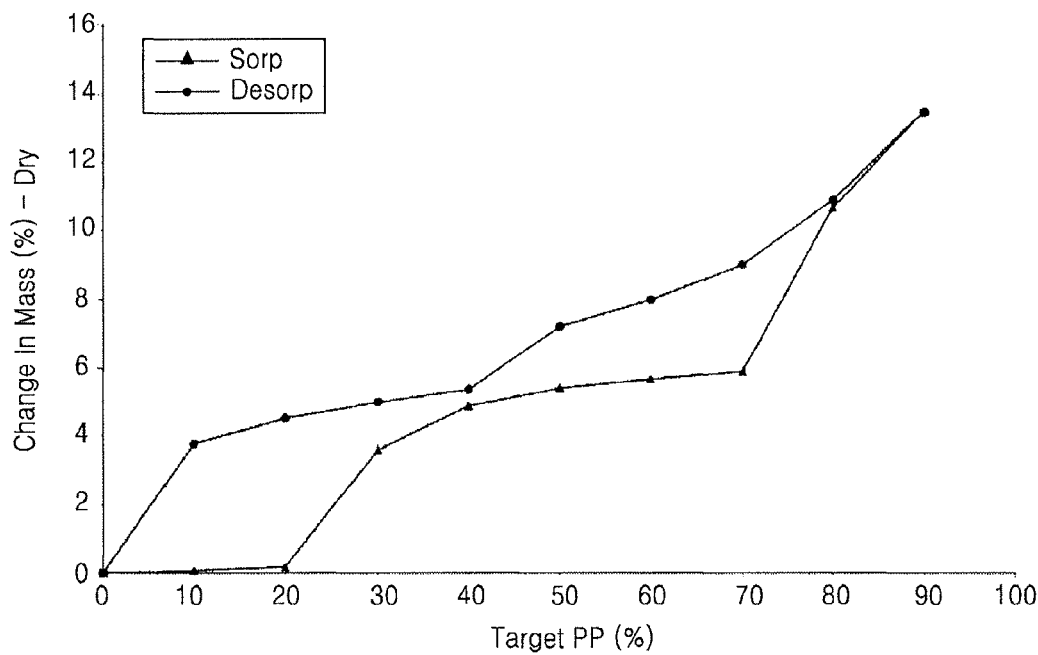

[Figure 3G]
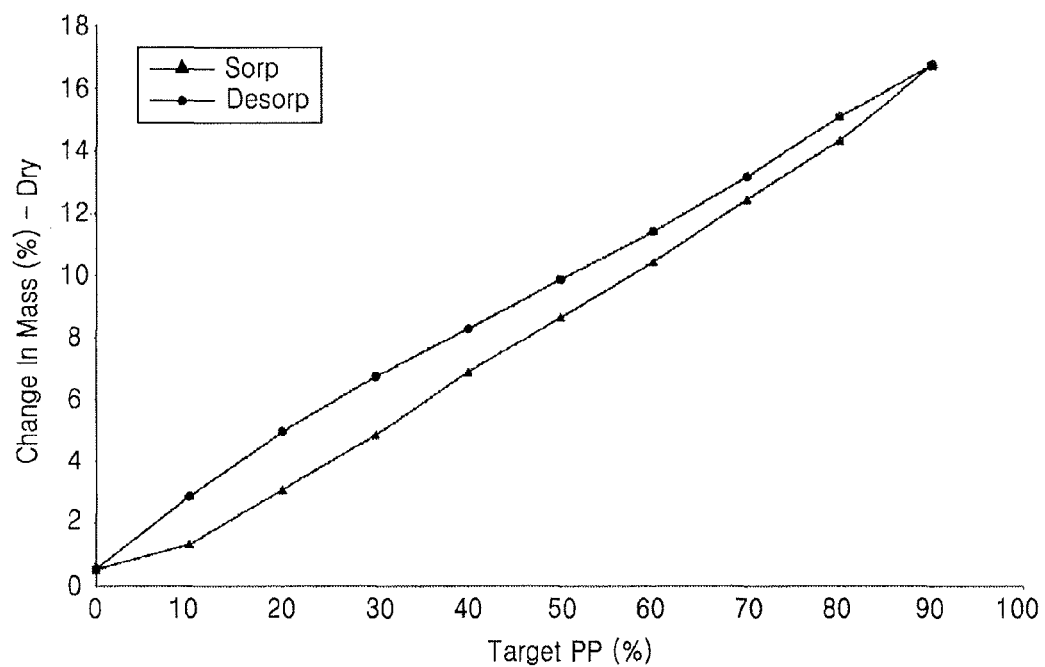

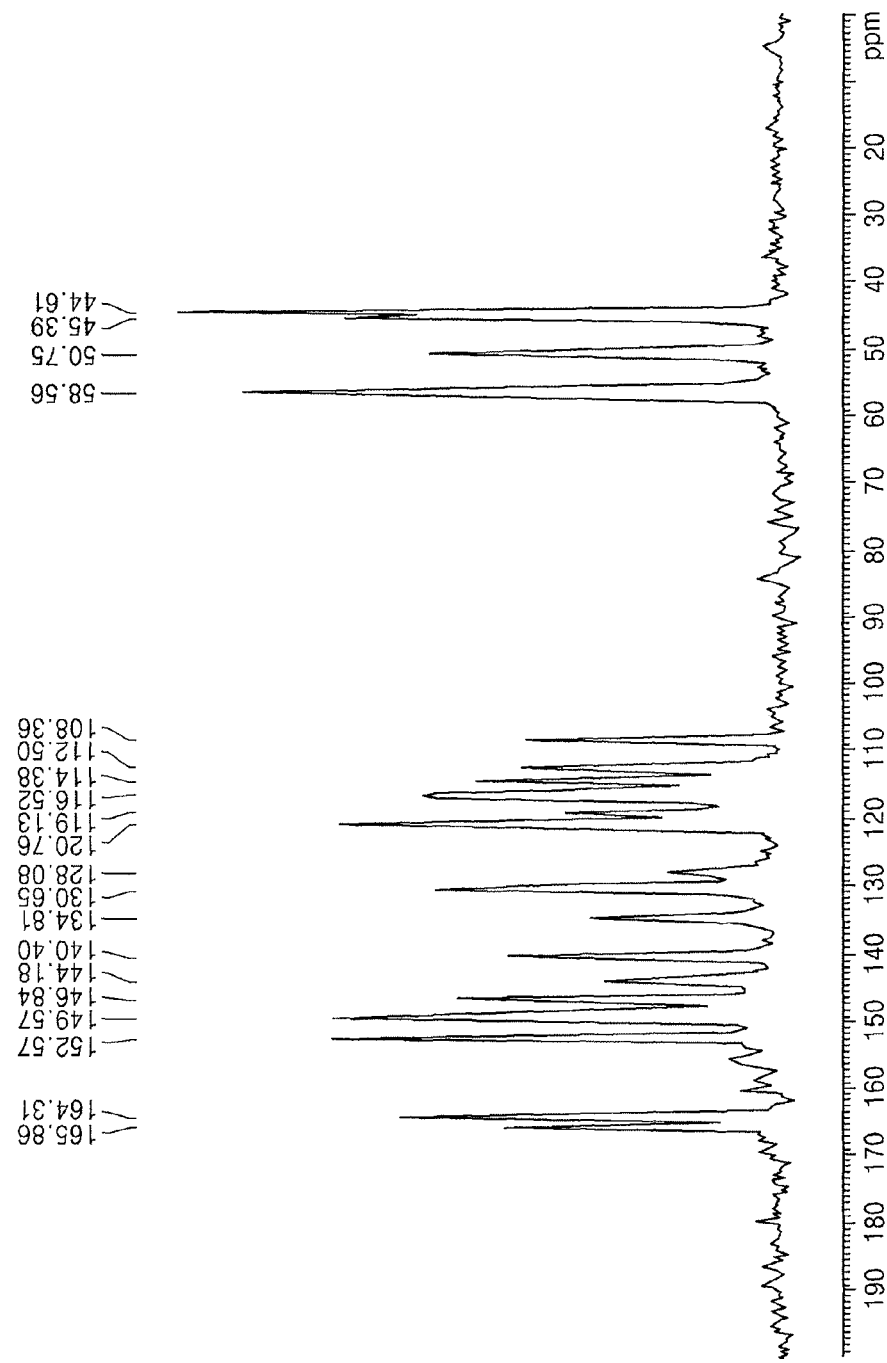
[Figure 4A]

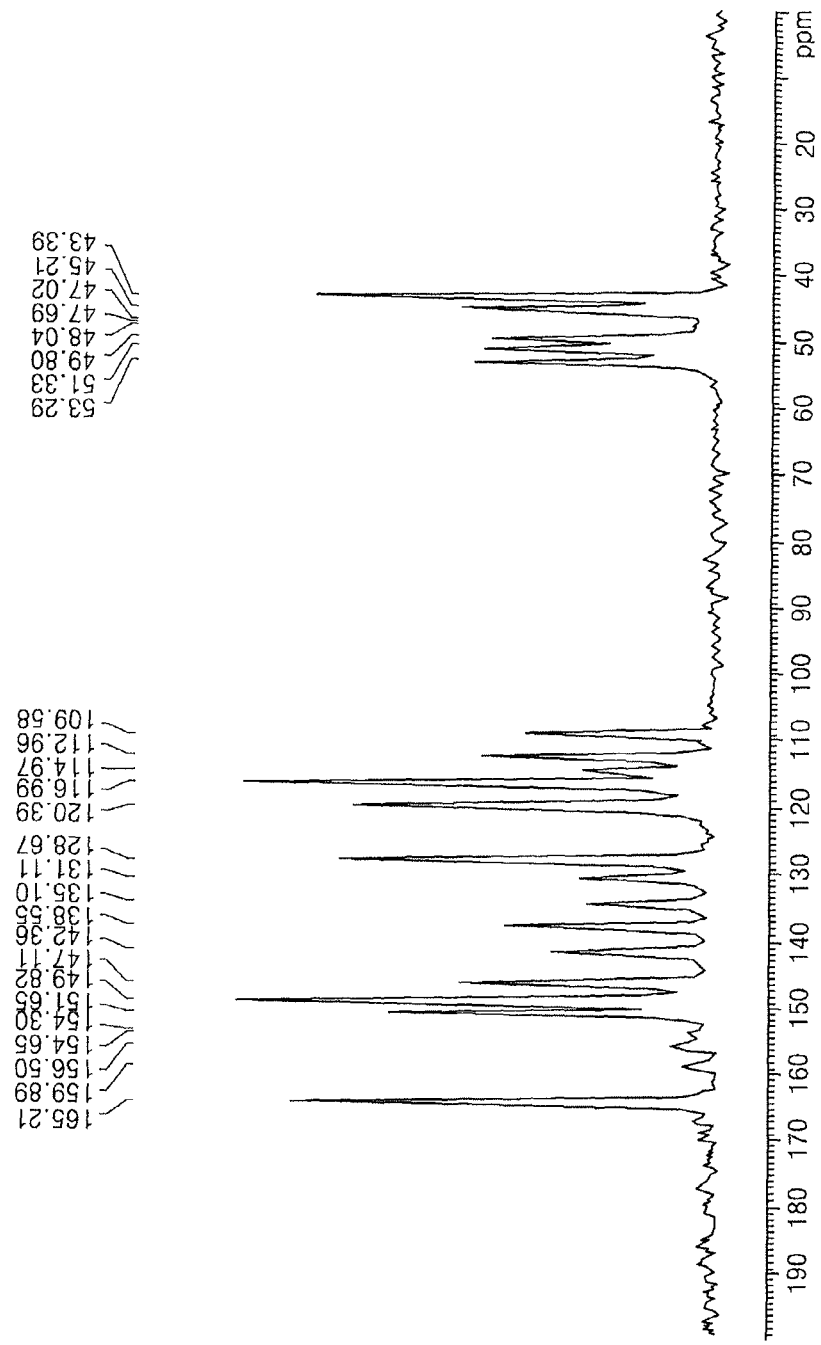
[Figure 4B]

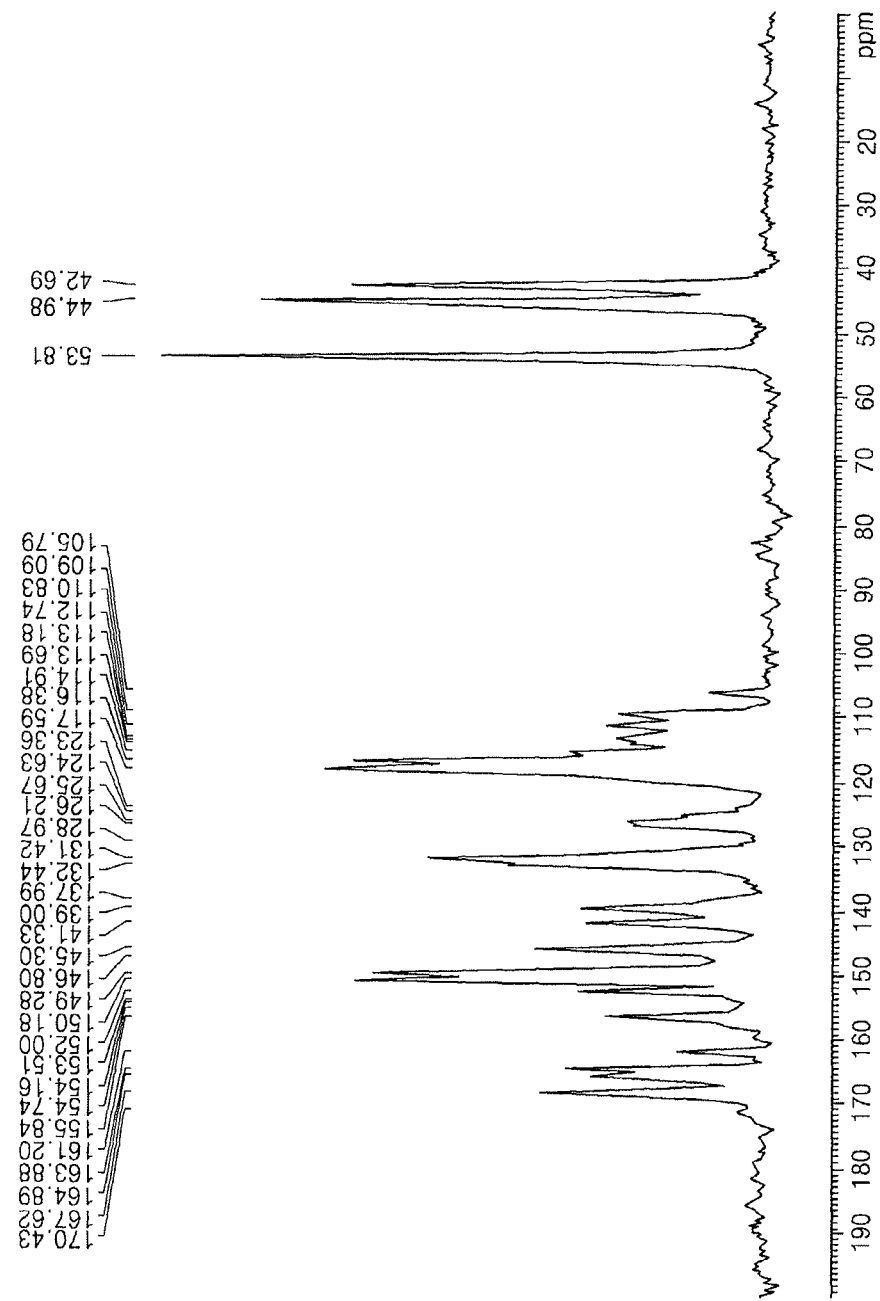
[Figure 4C]

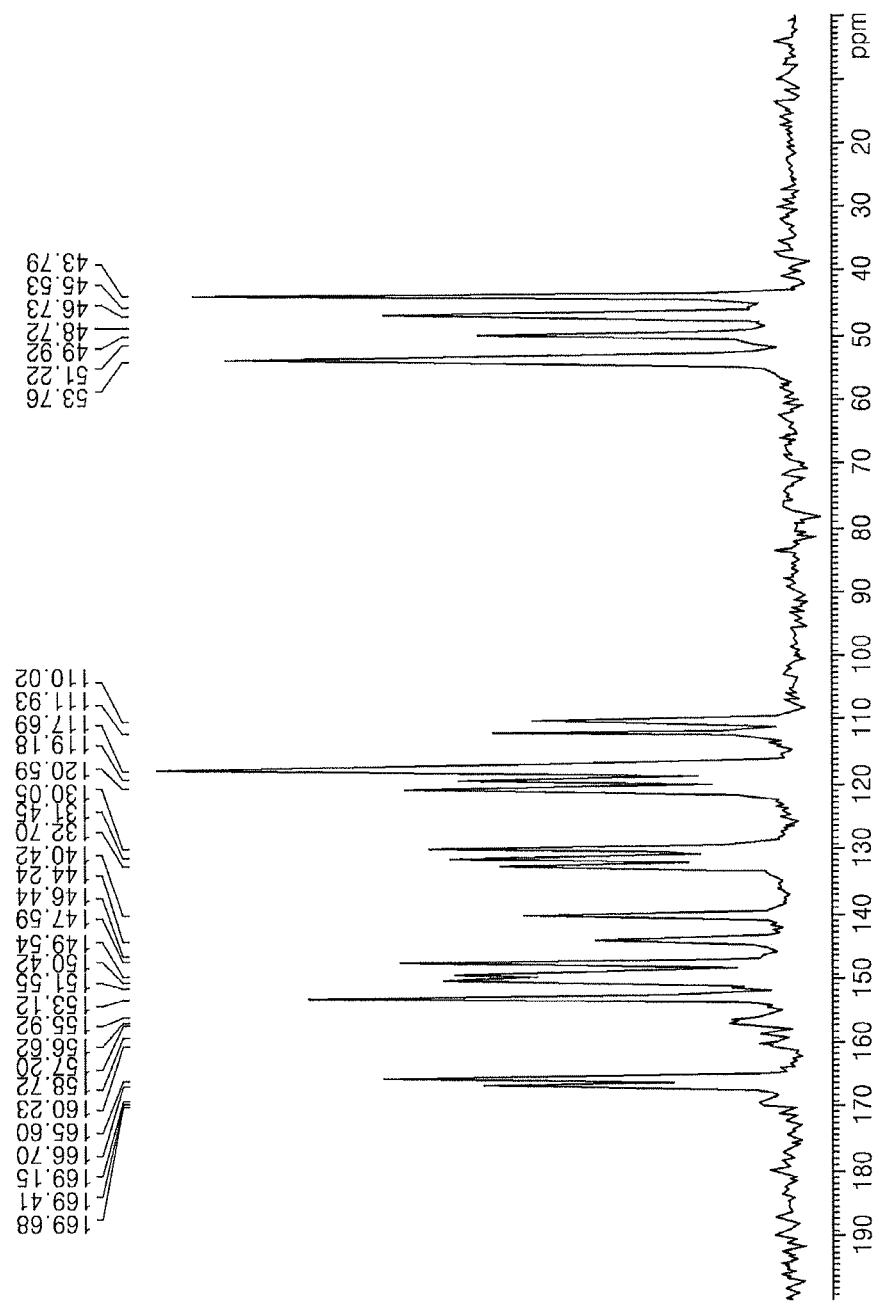
[Figure 4D]

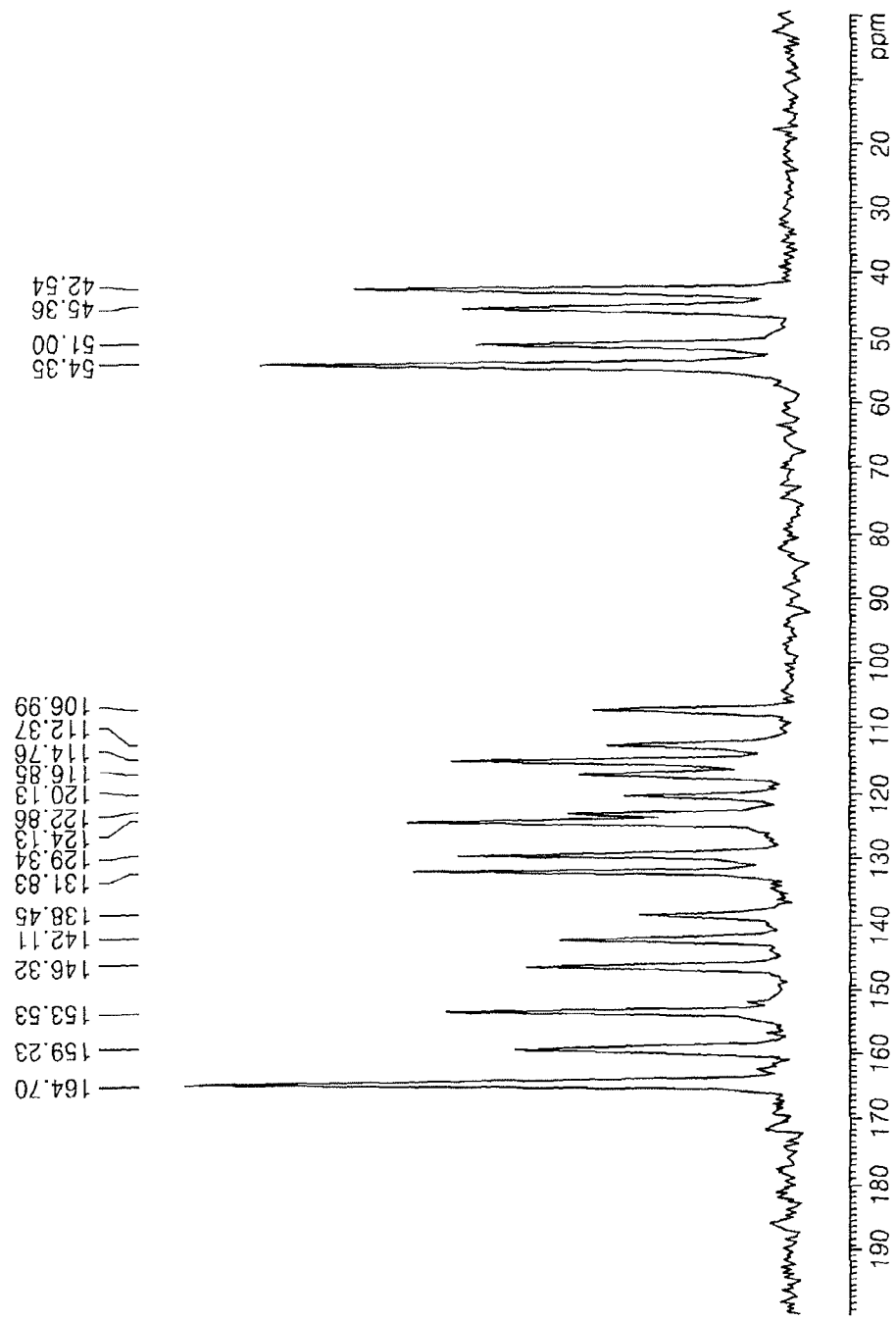
[Figure 4E]

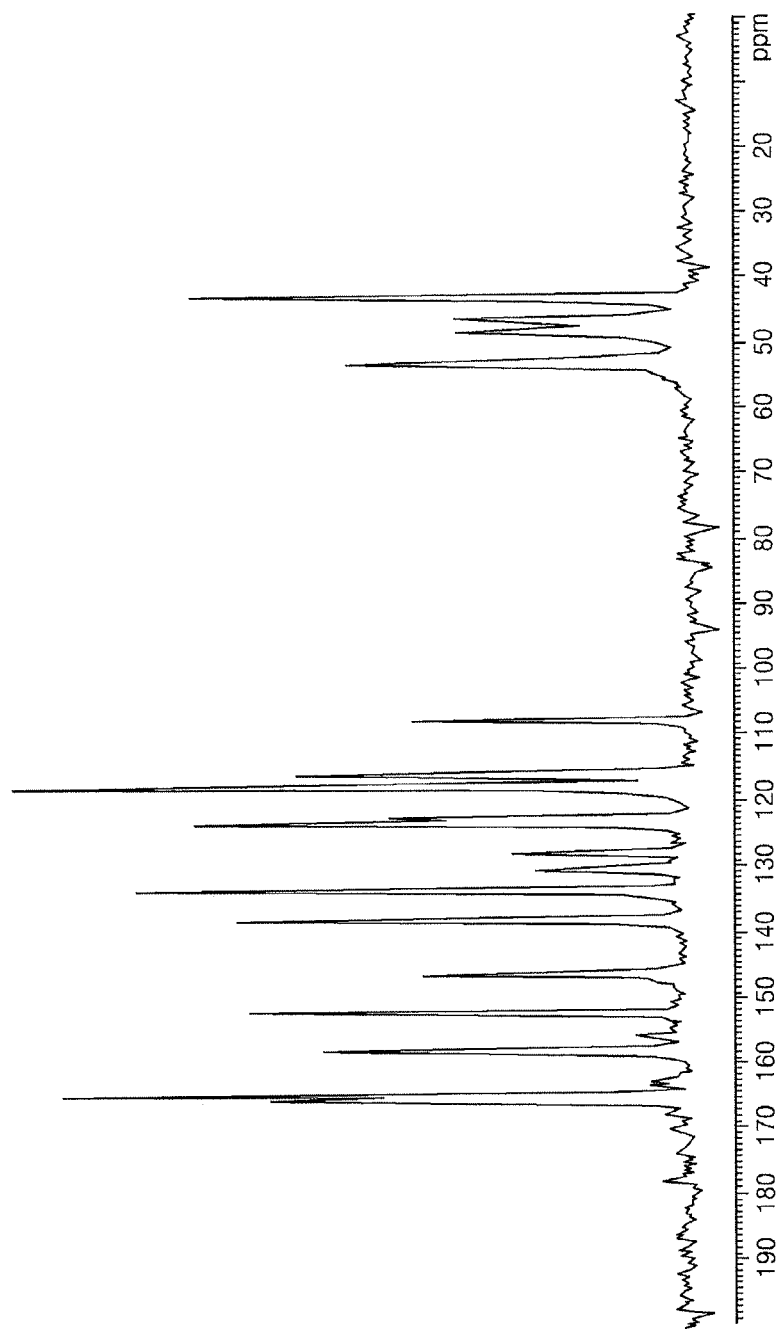
[Figure 4F]

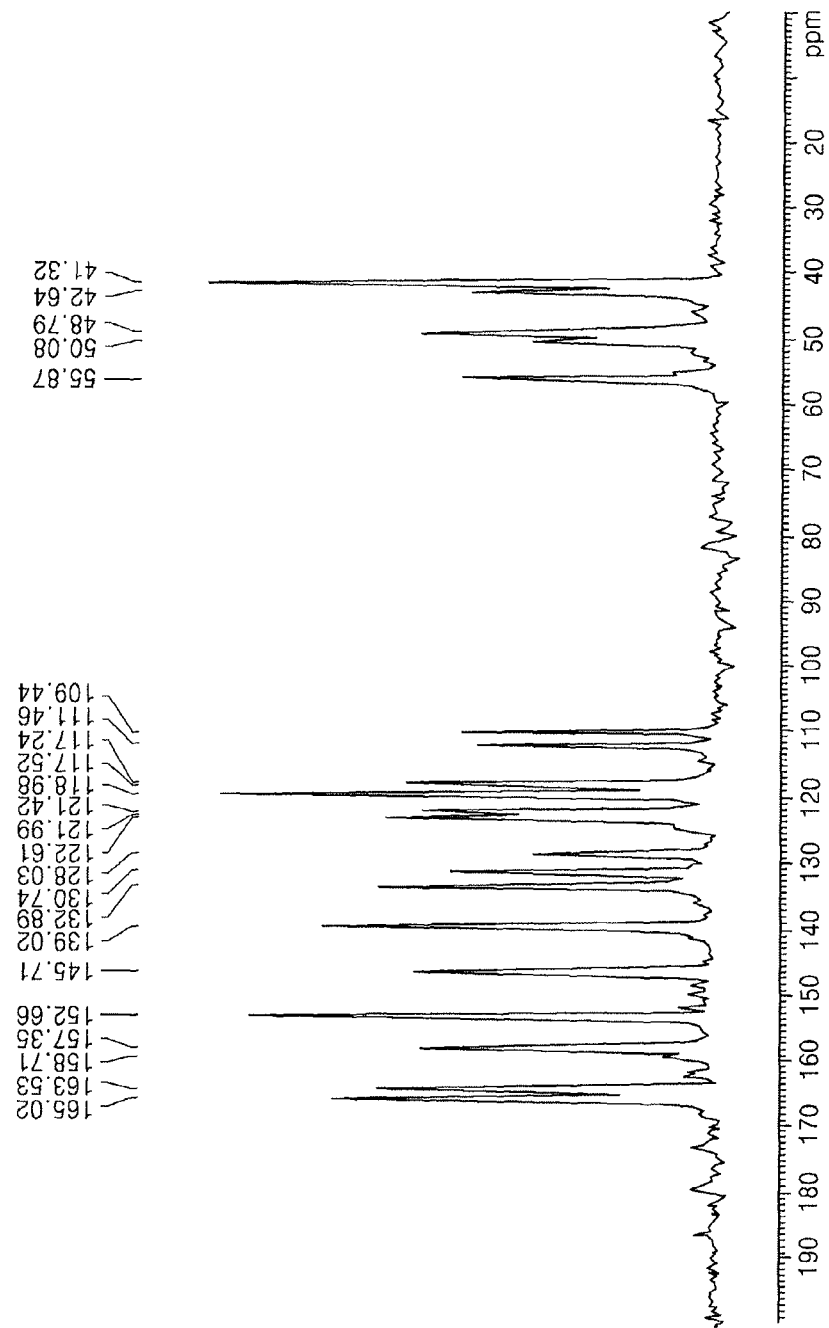
[Figure 4G]

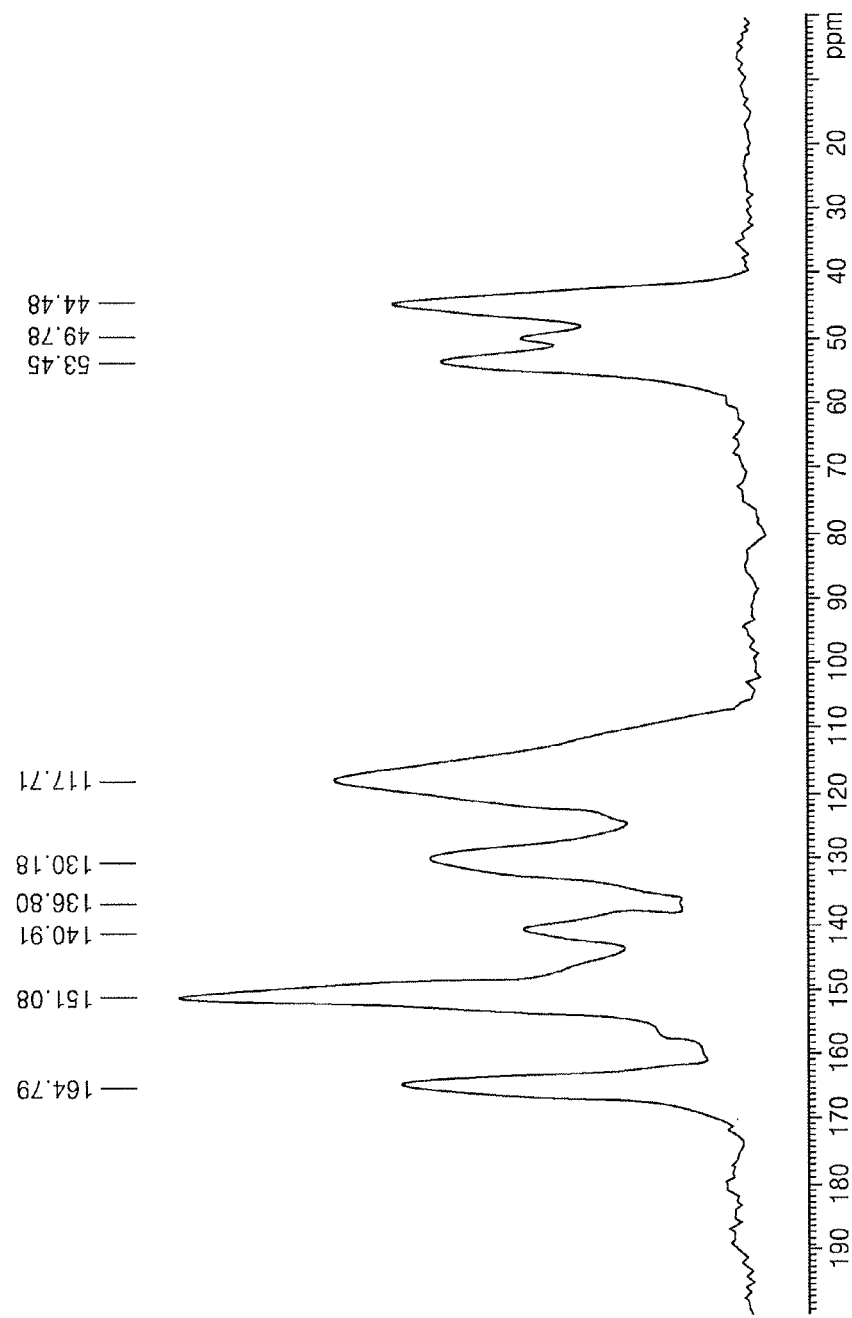
[Figure 4H]

CRYSTALLINE FORMS OF HYDROCHLORIDE SALTS OF THIENOPYRIMIDINE COMPOUND

CROSS REFERENCE TO RELATED APPLICATIONS

This application is a National Stage of International Application No. PCT/KR2016/015535, filed on Dec. 30, 2016, which claims priority from Korean Patent Application No. 10-2015-0190853, filed on Dec. 31, 2015 and Korean Patent Application No. 10-2016-0065977, filed on May 27, 2016.

TECHNICAL FIELD

The present invention relates to hydrochloride salts of a thienopyrimidine compound, and pharmaceutical compositions containing the same. More specifically, the present invention relates to hydrochloride salts of N-(3-(2-(4-(4-methylpiperazin-1-yl)phenylamino)thieno[3,2-d]pyrimidin-4-yloxy)phenyl)acrylamide, and pharmaceutical compositions containing the same.

BACKGROUND ART

The compound of Formula 1 below, whose compound name is N-(3-(2-(4-(4-methylpiperazin-1-yl)phenylamino)thieno[3,2-d]pyrimidin-4-yloxy)phenyl)acrylamide is disclosed in PCT application WO 2011/162515. The compound has a selective inhibitory activity for a mutant epidermal growth factor receptor tyrosine kinase.

[Formula 1]

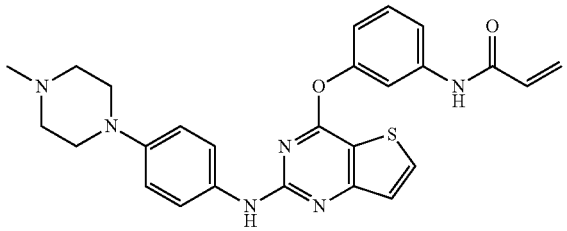

Additionally, the above reference discloses the method for preparing the compound of Formula 1.

However, the compound of Formula 1 prepared in the above cited reference was prepared as an amorphous solid, which is a form generally less suitable for large-scale production of pharmaceutical drugs. In addition, the rather poor solubility of the compound of Formula 1 obtainable by the method in the above cited reference left room for improvement.

Accordingly, there is a need for suitable solid forms, preferably crystalline forms, of the compound of Formula 1 that can fully comply with the strict requirements and details thereof regarding pharmaceutical solid forms and formulations while having improved water solubility.

One sort of solid forms are salt forms of active ingredients, e.g. acid addition salts of basic active ingredients obtainable by reaction with acids. It is a challenging endeavor to identify suitable salt forms with appropriate solid state properties as there are many salt formers and potentially several polymorphs for each salt form. The present inventors have discovered that hydrochloride salts of the compound of Formula 1, especially the crystalline forms thereof, have excellent overall physicochemical characteristics required pharmaceutically including, for example, enabling long-term stable maintenance without requiring particular storage conditions, etc., while having excellent water-solubility, thereby completing the present invention.

DISCLOSURE

Technical Problem

An object of the present invention is to provide a hydrochloride salt of the thienopyrimidine compound of Formula 1, and a pharmaceutical composition containing the same.

Technical Solution

To achieve the above object, in one aspect of the present invention, there is provided a hydrochloride salt, in particular a crystalline form of a hydrochloride salt, of the compound of Formula 1 shown below.

[Formula 1]

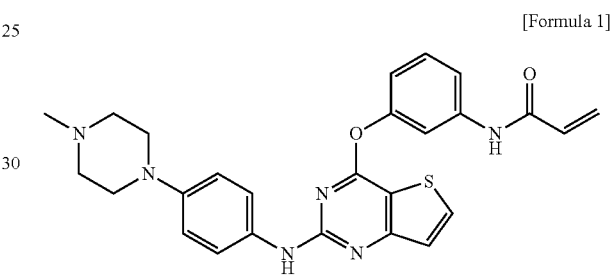

In a further aspect the crystalline form of the hydrochloride salt of the compound of Formula 1 is a monohydrochloride.

In a further aspect the crystalline form of the hydrochloride salt of the compound of Formula 1 is a dihydrochloride.

In a further aspect the crystalline form of the hydrochloride salt of the compound of Formula 1 is a hydrate.

In a further aspect the crystalline form of the hydrochloride salt of the compound of Formula 1 is a monohydrate.

In a further aspect the crystalline form of the hydrochloride salt of the compound of Formula 1 is a trihydrate.

In a further aspect the crystalline form of the hydrochloride salt of the compound of Formula 1 is a dihydrate.

Specific examples of the above crystalline forms are as shown below:

A crystalline form of a dihydrochloride hydrate, preferably a monohydrate (2HCl.1H$_2$O), of the compound of Formula 1 having an X-ray powder diffraction (XRPD) pattern comprising peaks at diffraction angles of 2θ=5.6°±0.2°, 21.1°±0.2° and 27.3°±0.2° when irradiated with a Cu—Kα light source. This crystalline form may further comprise diffraction peaks at 2θ=11.1°±0.2°, 14.0°±0.2° and 20.8°±0.2° when irradiated with a Cu—Kα light source;

A crystalline form of a dihydrochloride hydrate, preferably a monohydrate (2HCl.1H$_2$O), of the compound of Formula 1 having an X-ray powder diffraction (XRPD) pattern comprising peaks at diffraction angles of 2θ=6.4°±0.2°, 12.8°±0.2°, 20.8°±0.2° and 22.0°±0.2° when irradiated with a Cu—Kα light source. This crystalline form may further comprise diffraction peaks at 2θ=8.1°±0.2°, 9.7°±0.2°, 16.0°±0.2°, 24.1°±0.2°, 26.3°±0.2°, and 27.1°±0.2° when irradiated with a Cu—Kα light source;

A crystalline form of a dihydrochloride hydrate, preferably a trihydrate (2HCl.3H$_2$O), of the compound of Formula 1 having an X-ray powder diffraction (XRPD) pattern comprising peaks at diffraction angles of 2θ=4.6°±0.2°, 8.6°±0.2° and 15.8°±0.2° when irradiated with a Cu—Kα light source. This crystalline form may further comprise diffraction peaks at 2θ=17.2°±0.2°, 19.7°±0.2°, 25.1°±0.2°, and 26.3°±0.2° when irradiated with a Cu—Kα light source;

A crystalline form of a dihydrochloride hydrate, preferably a trihydrate (2HCl.3H$_2$O), of the compound of Formula 1 having an X-ray powder diffraction (XRPD) pattern comprising peaks at diffraction angles of 2θ=6.4°±0.2°, 7.0°±0.2°, 12.8°±0.2° and 21.0°±0.2° when irradiated with a Cu—Kα light source. This crystalline form may further comprise diffraction peaks at 2θ=15.5°±0.2°, 18.2°±0.2° and 27.9°±0.2° when irradiated with a Cu—Kα light source;

A crystalline form of a monohydrochloride hydrate, preferably a monohydrate (1HCl.1H$_2$O), of the compound of Formula 1 having an X-ray powder diffraction (XRPD) pattern comprising peaks at diffraction angles of 2θ=7.8°±0.2°, 22.5°±0.2° and 25.7°±0.2° when irradiated with a Cu—Kα light source. This crystalline form may further comprise diffraction peaks at 2θ=10.7°±0.2°, 13.0°±0.2°, 18.6°±0.2°, 19.1°±0.2°, 22.0°±0.2°, 24.6°±0.2° and 25.3°±0.2° when irradiated with a Cu—Kα light source;

A crystalline form of a monohydrochloride hydrate, preferably a dihydrate (1HCl.2H$_2$O), of the compound of Formula 1 having an X-ray powder diffraction (XRPD) pattern comprising peaks at diffraction angles of 2θ=7.5°±0.2°, 15.1°±0.2° and 20.0°±0.2° when irradiated with a Cu—Kα light source. This crystalline form may further comprise diffraction peaks at 2θ=21.2°±0.2° and 25.1°±0.2° when irradiated with a Cu—Kα light source;

A crystalline form of a monohydrochloride hydrate, preferably a dihydrate (1HCl.2H$_2$O), of the compound of Formula 1 having an X-ray powder diffraction (XRPD) pattern comprising peaks at diffraction angles of 2θ=8.7°±0.2°, 19.4°±0.2° and 23.1°±0.2° when irradiated with a Cu—Kα light source. This crystalline form may further comprise diffraction peaks at 2θ=11.6°±0.2°, 17.5°±0.2° and 26.1°±0.2° when irradiated with a Cu—Kα light source;

In a further aspect each crystalline form of the hydrochloride salt as described herein is in substantially pure form.

The term "substantially pure" as used herein means at least 95% pure, preferably 99% pure, where 95% pure means not more than 5%, and 99% pure means not more than 1%, of any other form of the compound of Formula 1 being present (other crystalline form, amorphous form, etc.).

In a further aspect of the present invention, there is provided a pharmaceutical composition containing a hydrochloride salt of the compound of Formula 1 or one of the crystalline forms of the hydrochloride salt as described herein and at least one pharmaceutically acceptable carrier and/or diluent.

The pharmaceutical composition can be used for the treatment of cancer induced by epidermal growth factor receptor tyrosine kinase or a mutant thereof.

Advantageous Effects

The hydrochloride salt of the compound of Formula 1, in particular the crystalline forms according to the present invention has excellent overall physicochemical characteristics, i.e., water solubility, hygroscopicity, chemical stability, etc., and thus they can be easily used for the preparation of a pharmaceutical composition containing the same as an active ingredient.

DESCRIPTION OF DRAWINGS

FIGS. 1A to 1G show X-ray powder diffraction (XRPD) patterns of crystalline forms of the salts of the compound of Formula 1 according to Examples of the present invention.

FIG. 1H shows an X-ray powder diffraction (XRPD) pattern of an amorphous form of the salts of the compound of Formula 1 according to Comparative Example of the present invention.

FIGS. 2A to 2F show graphs of differential scanning calorimetry (DSC) of crystalline forms of the salts of the compound of Formula 1 according to Examples of the present invention.

FIG. 2G shows a graph of differential scanning calorimetry (DSC) of an amorphous form of the salts of the compound of Formula 1 according to Comparative Example of the present invention.

FIGS. 3A to 3F show graphs of dynamic vapor sorption (DVS) of crystalline forms of the salts of the compound of Formula 1 according to Examples of the present invention.

FIG. 3G shows a graph of dynamic vapor sorption (DVS) of an amorphous form of the salts of the compound of Formula 1 according to Comparative Example of the present invention.

FIGS. 4A to 4G show graphs of $^{13}$C cross polarization/magic angle spinning total suppression of sidebands solid state nuclear magnetic resonance (CP/MAS TOSS ssNMR) of crystalline forms of the salts of the compound of Formula 1 according to Examples of the present invention.

FIG. 4H shows a graph of $^{13}$C CP/MAS TOSS ssNMR of an amorphous form of the salts of the compound of Formula 1 according to a Comparative Example of the present invention.

MODE FOR INVENTION

Unless otherwise defined, all terms including technical and scientific terms used herein have the same meaning as commonly understood within the context by one of ordinary skill in the art to which this invention belongs. However, unless otherwise specified, the term described below will have the meaning indicated below over the entire specification:

As used herein, the term "about" refers to being within 5% of a particular value or range, and preferably within 1% to 2%. For example, "about 10%" refers to 9.5% to 10.5%, and preferably, 9.8% to 10.2%. For another example, "about 100° C." refers to 95° C. to 105° C., and preferably, 98° C. to 102° C.

Unless otherwise specified, it must be apparent to a skilled practitioner that the values of peaks from X-ray powder diffraction studies reported in this invention are associated with experimental errors typically observable in this field. Specifically, a peak is interpreted as to be located within ±0.5° of the value reported herein. More specifically, a peak is interpreted as to be located within ±0.2° of the value reported herein.

Unless otherwise specified, it must be apparent to a skilled practitioner that the values of peaks from solid state nuclear magnetic resonance (ssNMR) studies reported in this invention are associated with experimental errors typically observable in this field. Specifically, a chemical shift is interpreted as to be located within ±0.5 ppm of the value reported herein. More specifically, a chemical shift is interpreted as to be located within ±0.2 ppm of the value reported herein.

Hydrochloride salts of the compound of Formula 1 The present invention provides a hydrochloride salt of the compound of Formula 1 below, i.e., N-(3-(2-(4-(4-methylpiperazin-1-yl)phenylamino)thieno[3,2-d]pyrimidin-4-yloxy)phenyl)acrylamide.

[Formula 1]

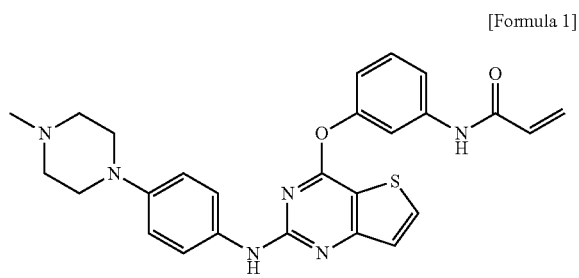 [SMILES: C=CC(=O)Nc1cccc(Oc2nc(Nc3ccc(N4CCN(C)CC4)cc3)nc3ccsc23)c1]

The compound of Formula 1 above (free base) may be prepared according to the conventional procedure described in WO 2011/162515, which is hereby incorporated by reference in its entirety.

The compound of Formula 1 disclosed in the above reference is in an amorphous form, and is a poorly soluble compound having water solubility below 0.1 μg/mL.

Generally, it is known that the conversion of a free base into a salt form can help solubilize a water-insoluble pharmaceutical material. However, the salt should also possess the overall physicochemical properties which are required pharmaceutically, such as reproducibility for the preparation of particular crystalline polymorphs, a high degree of crystallization, stability of crystalline forms, chemical stability, non-hygroscopicity, etc.

For the selection of an appropriate salt type for the compound of Formula 1, salts of the compound of Formula 1 were prepared using various acids and solvents according to various conditions and procedures, and the physicochemical properties of the thus-obtained salts were evaluated. Among the thus-obtained high number of salts and types of crystalline forms the hydrochloride salts of the compound of Formula 1, in particular the various crystalline forms described herein showed the best overall physicochemical properties which are required pharmaceutically, such as reproducibility for the preparation of particular crystalline polymorphs, a high degree of crystallization, stability of crystalline forms, chemical stability, non-hygroscopicity, etc.

In one embodiment of the present invention, provided are crystalline hydrochloride salts of the compound of Formula 1. In a particular embodiment of the present invention, these crystalline hydrochloride salts are hydrates. In another specific embodiment, the crystalline hydrochloride salt is dihydrochloride. In a further specific embodiment, this dihydrochloride salt is a hydrate. In yet another specific embodiment, the crystalline hydrochloride salt is monohydrochloride. In a still further specific embodiment, this monohydrochloride salt is a hydrate.

Crystalline Form of Salts of the Compound of Formula 1

The salts of the compound of Formula 1 may be prepared in a crystalline form, an amorphous form, or a mixture thereof, and preferably in a crystalline form. The crystalline form of a hydrochloride salt of the Formula 1 compound has excellent stability and is thus preferable in that it has a physicochemical property which facilitates its formulation.

According to the present invention, the compound of Formula 1 may be prepared in various crystalline forms of a hydrochloride, e.g., a crystalline form (Type A) of a dihydrochloride hydrate, preferably monohydrate ($2HCl.1H_2O$); a crystalline form (Type B) of a dihydrochloride hydrate, preferably monohydrate ($2HCl.1H_2O$); a crystalline form (Type A) of a dihydrochloride hydrate, preferably trihydrate ($2HCl.3H_2O$); a crystalline form (Type B) of a dihydrochloride hydrate, preferably trihydrate ($2HCl.3H_2O$); a crystalline form of a monohydrochloride hydrate, preferably monohydrate ($1HCl.1H_2O$); a crystalline form (Type A) of a monohydrochloride hydrate, preferably dihydrate ($1HCl.2H_2O$); and a crystalline form (Type B) of a monohydrochloride hydrate, preferably dihydrate ($1HCl.2H_2O$).

Among the crystalline forms of hydrochloride salts, as examined in Test Example 1 described later, the crystalline form (Type A) of the dihydrochloride hydrate, preferably monohydrate ($2HCl.1H_2O$), showed the highest water solubility, and it may be advantageous from the aspects of non-hygroscopicity/non-dehumidification and stability, and thus may be preferable as an active ingredient for a pharmaceutical composition.

Each of the crystalline forms according to the present invention will be explained more specifically herein below.

In an exemplary embodiment (ex. 1), the present invention provides a crystalline form (Type A) of a dihydrochloride hydrate, preferably monohydrate ($2HCl.1H_2O$), of the compound of Formula 1.

This crystalline form (ex. 1) exhibits an XRPD pattern comprising peaks at diffraction angles of $2\theta=5.6°\pm0.2°$ and $27.3°\pm0.2°$ when irradiated with a Cu—Kα light source (XRPD1-1).

More specifically, the above crystalline form (ex. 1) exhibits an XRPD pattern comprising peaks at diffraction angles of $2\theta=5.6°\pm0.2°$, $21.1°\pm0.2°$ and $27.3°\pm0.2°$ when irradiated with a Cu—Kα light source (XRPD1-2).

More specifically, the above crystalline form (ex. 1) has an XRPD pattern comprising peaks at diffraction angles of $2\theta=5.6°\pm0.2°$, $11.1°\pm0.2°$ and $27.3°\pm0.2°$ when irradiated with a Cu—Kα light source (XRPD1-3).

More specifically, the above crystalline form (ex. 1) has an XRPD pattern comprising peaks at diffraction angles of $2\theta=5.6°\pm0.2°$, $11.1°\pm0.2°$, $21.1°\pm0.2°$, and $27.3°\pm0.2°$ when irradiated with a Cu—Kα light source (XRPD1-4).

More specifically, the above crystalline form (ex. 1) has an XRPD pattern comprising peaks at diffraction angles of $2\theta=5.6°\pm0.2°$, $11.1°\pm0.2°$, $14.0°\pm0.2°$ and $27.3°\pm0.2°$ when irradiated with a Cu—Kα light source (XRPD1-5).

More specifically, the above crystalline form (ex. 1) has an XRPD pattern comprising peaks at diffraction angles of $2\theta=5.6°\pm0.2°$, $11.1°\pm0.2°$, $14.0°\pm0.2°$, $20.8°\pm0.2°$, and $27.3°\pm0.2°$ when irradiated with a Cu—Kα light source (XRPD1-6).

More specifically, the above crystalline form (ex. 1) has an XRPD pattern comprising peaks at diffraction angles of $2\theta=5.6°\pm0.2°$, $11.1°\pm0.2°$, $14.0°\pm0.2°$, $20.8°\pm0.2°$, $21.1°\pm0.2°$, and $27.3°\pm0.2°$ when irradiated with a Cu—Kα light source (XRPD1-7).

More specifically, the above crystalline form (ex. 1) has an XRPD pattern comprising peaks at diffraction angles of $2\theta=5.6°\pm0.2°$, $10.7°\pm0.2°$, $11.1°\pm0.2°$, $14.0°\pm0.2°$, $20.8°\pm0.2°$, $21.1°\pm0.2°$, $22.5°\pm0.2°$, and $27.3°\pm0.2°$ when irradiated with a Cu—Kα light source (XRPD1-8).

These peaks may be those having a relative intensity (I/Io) of about 10% or more.

The above crystalline form (ex. 1) may have a water content of about 3.1% (theoretical water content value of 3.11%) and a melting point of about 202° C. to 225° C.

The above crystalline form (ex. 1) may have a broad endothermic peak in the range of 25-150° C. and an endothermic peak(s) at about 221° C. by a DSC with a heating rate of 10° C./min.

The above crystalline form (ex. 1) may have an endothermic peak which has a starting point at about 49° C. and its lowest point at about 110° C., endothermic peaks at about 221° C. and about 253° C., and an exothermic peak at about 265° C. in a DSC (10° C./min).

The above crystalline form (ex. 1) may show reversible water sorption and desorption about 3% in the complete range of 0-90% RH, with a very low level of change in the region with a relative humidity of 10% to 90% in a DVS.

The above crystalline form (ex. 1) may have a $^{13}$C CP/MAS TOSS ssNMR spectrum comprising peaks at the following $^{13}$C chemical shifts: 44.6±0.2 ppm and 56.6±0.2 ppm (ssNMR1-1).

More specifically, the above crystalline form (ex. 1) may have a $^{13}$C CP/MAS TOSS ssNMR spectrum comprising peaks at the following $^{13}$C chemical shifts: 44.6±0.2 ppm, 45.4±0.2 ppm, 50.8±0.2 ppm and 56.6±0.2 ppm (ssNMR1-2).

The above crystalline form (ex. 1) may have a $^{13}$C CP/MAS TOSS ssNMR spectrum comprising peaks at the following $^{13}$C chemical shifts: 149.6±0.2 ppm, 152.6±0.2 ppm and 164.3±0.2 ppm (ssNMR1-3).

More specifically, the above crystalline form (ex. 1) may have a $^{13}$C CP/MAS TOSS ssNMR spectrum comprising peaks at the following $^{13}$C chemical shifts: 116.5±0.2 ppm, 130.7±0.2 ppm, 146.8±0.2 ppm, 149.6±0.2 ppm, 152.6±0.2 ppm and 164.3±0.2 ppm (ssNMR1-4).

More specifically, the above crystalline form (ex. 1) may have a $^{13}$C CP/MAS TOSS ssNMR spectrum comprising peaks at the following $^{13}$C chemical shifts: 44.6±0.2 ppm, 56.6±0.2 ppm, 149.6±0.2 ppm, 152.6±0.2 ppm and 164.3±0.2 ppm (ssNMR1-5).

The above crystalline form (ex. 1) may have
(a) an X-ray powder diffraction (XRPD) pattern comprising peaks at diffraction angle 2θ values of 5.6°±0.2° and 27.3°±0.2° when irradiated with a Cu—Kα light source; and
(b) a $^{13}$C CP/MAS TOSS ssNMR spectrum comprising peaks at the following $^{13}$C chemical shifts: 44.6±0.2 ppm and 56.6±0.2 ppm.

The above crystalline form (ex. 1) may have
(a) an X-ray powder diffraction (XRPD) pattern comprising peaks at diffraction angle 2θ values of 5.6°±0.2° and 27.3°±0.2° when irradiated with a Cu—Kα light source; and
(b) a $^{13}$C CP/MAS TOSS ssNMR spectrum comprising peaks at the following $^{13}$C chemical shifts: 149.6±0.2 ppm, 152.6±0.2 ppm and 164.3±0.2 ppm.

The above crystalline form (ex. 1) may also be characterized by any other combination of lists of XRPD peaks (XRPD1-1 to XRPD1-7) and $^{13}$C chemical shifts (ssNMR1-1 to ssNMR1-5) as listed above.

In another exemplary embodiment (ex. 2), the present invention also provides a crystalline form (Type B) of a dihydrochloride hydrate, preferably monohydrate (2HCl.1H$_2$O), of the compound of Formula 1.

This crystalline form (ex. 2) exhibits an XRPD pattern comprising peaks at diffraction angles of 2θ=6.4°±0.2°, 12.8°±0.2°, 20.8°±0.2° and 22.0°±0.2° when irradiated with a Cu—Kα light source (XRPD2-1).

More specifically, the above crystalline form (ex. 2) has an XRPD pattern comprising peaks at diffraction angles of 2θ=6.4°±0.2°, 8.1°±0.2°, 9.7°±0.2°, 12.8°±0.2°, 16.0°±0.2°, 20.8°±0.2°, 22.0°±0.2°, 24.1°±0.2°, 26.3°±0.2°, and 27.1°±0.2° when irradiated with a Cu—Kα light source (XRPD2-2).

More specifically, the above crystalline form (ex. 2) has an XRPD pattern comprising peaks at diffraction angles of 2θ=6.4°±0.2°, 8.1°±0.2°, 9.7°±0.2°, 12.8°±0.2°, 16.0°±0.2°, 20.8°±0.2°, 22.0°±0.2°, 24.1°±0.2°, 26.3°±0.2°, 26.8°±0.2°, 27.1°±0.2°, and 28.1°±0.2° when irradiated with a Cu—Kα light source (XRPD2-3).

These peaks may be those having a relative intensity of about 20% or more.

The above crystalline form (ex. 2) may have a $^{13}$C CP/MAS TOSS ssNMR spectrum comprising peaks at the following $^{13}$C chemical shifts: 43.4±0.2 ppm and 45.2±0.2 ppm (ssNMR2-1).

More specifically, the above crystalline form (ex. 2) may have a $^{13}$C CP/MAS TOSS ssNMR spectrum comprising peaks at the following $^{13}$C chemical shifts: 43.4±0.2 ppm, 45.2±0.2 ppm, 49.8±0.2 ppm, 51.3±0.2 ppm and 53.3±0.2 ppm (ssNMR2-2).

The above crystalline form (ex. 2) may have a $^{13}$C CP/MAS TOSS ssNMR spectrum comprising peaks at the following $^{13}$C chemical shifts: 117.0±0.2 ppm, 149.8±0.2 ppm and 165.2±0.2 ppm (ssNMR2-3).

More specifically, the above crystalline form (ex. 2) may have a $^{13}$C CP/MAS TOSS ssNMR spectrum comprising peaks at the following $^{13}$C chemical shifts: 117.0±0.2 ppm, 120.4±0.2 ppm, 128.7±0.2 ppm, 149.8±0.2 ppm, 151.7±0.2 ppm and 165.2±0.2 ppm (ssNMR2-4).

More specifically, the above crystalline form (ex. 2) may have a $^{13}$C CP/MAS TOSS ssNMR spectrum comprising peaks at the following $^{13}$C chemical shifts: 43.4±0.2 ppm, 45.2±0.2 ppm, 117.0±0.2 ppm, 149.8±0.2 ppm and 165.2±0.2 ppm (ssNMR2-5).

The above crystalline form (ex. 2) may have
(a) an X-ray powder diffraction (XRPD) pattern comprising peaks at diffraction angle 2θ values of 6.4°±0.2°, 12.8°±0.2°, 20.8°±0.2° and 22.0°±0.2° when irradiated with a Cu—Kα light source; and
(b) a $^{13}$C CP/MAS TOSS ssNMR spectrum comprising peaks at the following $^{13}$C chemical shifts: 43.4±0.2 ppm and 45.2±0.2 ppm.

The above crystalline form (ex. 2) may have
(a) an X-ray powder diffraction (XRPD) pattern comprising peaks at diffraction angle 2θ values of 6.4°±0.2°, 12.8°±0.2°, 20.8°±0.2° and 22.0°±0.2° when irradiated with a Cu—Kα light source; and
(b) a $^{13}$C CP/MAS TOSS ssNMR spectrum comprising peaks at the following $^{13}$C chemical shifts: 117.0±0.2 ppm, 149.8±0.2 ppm and 165.2±0.2 ppm.

The above crystalline form (ex. 2) may also be characterized by any other combination of lists of XRPD peaks (XRPD2-1 to XRPD2-3) and $^{13}$C chemical shifts (ssNMR2-1 to ssNMR2-5) as listed above.

In another exemplary embodiment (ex. 3), the present invention also provides a crystalline form (Type A) of a dihydrochloride hydrate, preferably trihydrate (2HCl.3H$_2$O), of the compound of Formula 1.

This crystalline form (ex. 3) exhibits an XRPD pattern comprising peaks at diffraction angles of 2θ=4.6°±0.2°, 8.6°±0.2° and 15.8°±0.2° when irradiated with a Cu—Kα light source (XRPD3-1).

More specifically, the above crystalline form (ex. 3) has an XRPD pattern comprising peaks at diffraction angles of 2θ=4.6°±0.2°, 8.6°±0.2°, 15.8°±0.2°, 17.2°±0.2°, 19.7°±0.2°, 25.1°±0.2°, and 26.3°±0.2° when irradiated with a Cu—Kα light source (XRPD3-2).

More specifically, the above crystalline form (ex. 3) has an XRPD pattern comprising peaks at diffraction angles of 2θ=4.6°±0.2°, 8.6°±0.2°, 15.8°±0.2°, 17.2°±0.2°, 19.7°±0.2°, 20.1°±0.2°, 21.1°±0.2°, 23.5°±0.2°, 25.1°±0.2°, and 26.3°±0.2° when irradiated with a Cu—Kα light source (XRPD3-3).

These peaks may be those having a relative intensity of about 15% or more.

The above crystalline form (ex. 3) may have endothermic peaks at about 51° C. and about 95° C. (10° C./min) and endothermic peaks at about 178° C. and about 218° C. in a DSC (10° C./min).

The above crystalline form (ex. 3) may have a water content of about 10.1% (theoretical water content value of 8.8%) and a melting point of about 205° C. to 210° C.

The above crystalline form (ex. 3) may have a hygroscopicity measured at a very low level in the region with a relative humidity of 10% to 40% in a DVS, but the hygroscopicity in the region with a relative humidity of 40% or higher may be measured to be about 9%.

The above crystalline form (ex. 3) may have a $^{13}C$ CP/MAS TOSS ssNMR spectrum comprising peaks at the following $^{13}C$ chemical shifts: 45.0±0.2 ppm and 53.8±0.2 ppm (ssNMR3-1).

More specifically, the above crystalline form (ex. 3) may have a $^{13}C$ CP/MAS TOSS ssNMR spectrum comprising peaks at the following $^{13}C$ chemical shifts: 116.4±0.2 ppm, 117.6±0.2 ppm, 131.4±0.2 ppm, 149.3±0.2 ppm, and 150.2±0.2 ppm (ssNMR3-2).

The above crystalline form (ex. 3) may have a $^{13}C$ CP/MAS TOSS ssNMR spectrum comprising peaks at the following $^{13}C$ chemical shifts: 117.6±0.2 ppm and 150.2±0.2 ppm (ssNMR3-3).

More specifically, the above crystalline form (ex. 3) may have a $^{13}C$ CP/MAS TOSS ssNMR spectrum comprising peaks at the following $^{13}C$ chemical shifts: 116.4±0.2 ppm, 117.6±0.2 ppm, 131.4±0.2 ppm, 149.3±0.2 ppm, and 150.2±0.2 ppm (ssNMR3-4).

More specifically, the above crystalline form (ex. 3) may have a $^{13}C$ CP/MAS TOSS ssNMR spectrum comprising peaks at the following $^{13}C$ chemical shifts: 45.0±0.2 ppm, 53.8±0.2 ppm, 117.6±0.2 ppm and 150.2±0.2 ppm (ssNMR3-5).

The above crystalline form (ex. 3) may have
(a) an X-ray powder diffraction (XRPD) pattern comprising peaks at diffraction angle 2θ values of 4.6°±0.2°, 8.6°±0.2°, and 15.8°±0.2° when irradiated with a Cu—Kα light source; and
(b) a $^{13}C$ solid state NMR spectrum comprising peaks at the following $^{13}C$ chemical shifts: 45.0±0.2 ppm and 53.8±0.2 ppm.

The above crystalline form (ex. 3) may have
(a) an X-ray powder diffraction (XRPD) pattern comprising peaks at diffraction angle 2θ values of 4.6°±0.2°, 8.6°±0.2°, and 15.8°±0.2° when irradiated with a Cu—Kα light source; and
(b) a $^{13}C$ solid state NMR spectrum comprising peaks at the following $^{13}C$ chemical shifts: 117.6±0.2 ppm and 150.2±0.2 ppm.

The above crystalline form (ex. 3) may also be characterized by any other combination of lists of XRPD peaks (XRPD3-1 to XRPD3-3) and $^{13}C$ chemical shifts (ssNMR3-1 to ssNMR3-5) as listed above.

In another exemplary embodiment (ex. 4), the present invention also provides a crystalline form (Type B) of a dihydrochloride hydrate, preferably trihydrate ($2HCl\cdot 3H_2O$), of the compound of Formula 1.

This crystalline form (ex. 4) exhibits an XRPD pattern comprising peaks at diffraction angles of 2θ=6.4°±0.2°, 7.0°±0.2°, 12.8°±0.2° and 21.0°±0.2° when irradiated with a Cu—Kα light source (XRPD4-1).

More specifically, the above crystalline form (ex. 4) has an XRPD pattern comprising peaks at diffraction angles of 2θ=6.4°±0.2°, 7.0°±0.2°, 12.8°±0.2°, 15.5°±0.2°, 18.2°±0.2°, 21.0°±0.2°, and 27.9°±0.2° when irradiated with a Cu—Kα light source (XRPD4-2).

More specifically, the above crystalline form (ex. 4) has an XRPD pattern comprising peaks at diffraction angles of 2θ=6.4°±0.2°, 7.0°±0.2°, 12.8°±0.2°, 13.2°±0.2°, 14.1°±0.2°, 15.5°±0.2°, 18.2°±0.2°, 19.4°±0.2°, 20.5°±0.2°, 21.0°±0.2°, 23.0°±0.2°, 24.5°±0.2°, 25.8°±0.2°, and 27.9°±0.2° when irradiated with a Cu—Kα light source (XRPD4-3).

These peaks may be those having a relative intensity of about 20% or more.

The above crystalline form (ex. 4) may have an endothermic peak which has a starting point at about 50° C. and its lowest point at about 73° C., an endothermic peak at about 189° C., and an endothermic peak at about 222° C. in a DSC (10° C./min).

The above crystalline form (ex. 4) may have a water content of about 8.9% (theoretical water content value of 8.8%) and a melting point of about 210° C. to 215° C.

The above crystalline form (ex. 4) shows a hygroscopicity increase of about 6% in the region with a relative humidity of 10% to 30%, but the hygroscopicity in the region with a relative humidity of 40% or higher may be measured at a very low and constant level.

The above crystalline form (ex. 4) may have a $^{13}C$ CP/MAS TOSS ssNMR spectrum comprising peaks at the following $^{13}C$ chemical shifts: 43.8±0.2 ppm and 53.8±0.2 ppm (ssNMR4-1).

More specifically, the above crystalline form (ex. 4) may have a $^{13}C$ CP/MAS TOSS ssNMR spectrum comprising peaks at the following $^{13}C$ chemical shifts: 43.8±0.2 ppm, 46.7±0.2 ppm, 49.9±0.2 ppm and 53.8±0.2 ppm (ssNMR4-2).

The above crystalline form (ex. 4) may have a $^{13}C$ CP/MAS TOSS ssNMR spectrum comprising peaks at the following $^{13}C$ chemical shifts: 117.7±0.2 ppm, 153.1±0.2 ppm and 165.6±0.2 ppm (ssNMR4-3).

More specifically, the above crystalline form (ex. 4) may have a $^{13}C$ CP/MAS TOSS ssNMR spectrum comprising peaks at the following $^{13}C$ chemical shifts: 117.7±0.2 ppm, 120.6±0.2 ppm, 130.0±0.2 ppm, 147.6±0.2 ppm, 153.1±0.2 ppm and 165.6±0.2 ppm (ssNMR4-4).

More specifically, the above crystalline form (ex. 4) may have a $^{13}C$ CP/MAS TOSS ssNMR spectrum comprising peaks at the following $^{13}C$ chemical shifts: 43.8±0.2 ppm, 53.8±0.2 ppm, 117.7±0.2 ppm, 153.1±0.2 ppm and 165.6±0.2 ppm (ssNMR4-5).

The above crystalline form (ex. 4) may have
(a) an X-ray powder diffraction (XRPD) pattern comprising peaks at diffraction angle 2θ values of 6.4°±0.2°, 7.0°±0.2°, 12.8°±0.2° and 21.0°±0.2° when irradiated with a Cu—Kα light source; and (b) a $^{13}$C solid state NMR spectrum comprising peaks at the following $^{13}$C chemical shifts: 43.8±0.2 ppm and 53.8±0.2 ppm.

The above crystalline form (ex. 4) may have
(a) an X-ray powder diffraction (XRPD) pattern comprising peaks at diffraction angle 2θ values of 6.4°±0.2°, 7.0°±0.2°, 12.8°±0.2° and 21.0°±0.2° when irradiated with a Cu—Kα light source; and
(b) a $^{13}$C solid state NMR spectrum comprising peaks at the following $^{13}$C chemical shifts: 117.7±0.2 ppm, 153.1±0.2 ppm and 165.6±0.2 ppm.

The above crystalline form (ex. 4) may also be characterized by any other combination of lists of XRPD peaks (XRPD4-1 to XRPD4-3) and $^{13}$C chemical shifts (ssNMR4-1 to ssNMR4-5) as listed above.

In another exemplary embodiment (ex. 5), the present invention also provides a crystalline form of a monohydrochloride hydrate, preferably monohydrate (1HCl.1H$_2$O), of the compound of Formula 1.

This crystalline form (ex. 5) exhibits an XRPD pattern comprising peaks at diffraction angles of 2θ=7.8°±0.2°, 22.5°±0.2° and 25.7°±0.2° when irradiated with a Cu—Kα light source.

More specifically, the above crystalline form (ex. 5) has an XRPD pattern comprising peaks at diffraction angles of 2θ=7.8°±0.2°, 10.7°±0.2°, 13.0°±0.2°, 18.6°±0.2°, 19.1°±0.2°, 22.0°±0.2°, 22.5°±0.2°, 24.6°±0.2°, 25.3°±0.2°, and 25.7°±0.2° when irradiated with a Cu—Kα light source (XRPD5-2).

More specifically, the above crystalline form (ex. 5) has an XRPD pattern comprising peaks at diffraction angles of 2θ=7.8°±0.2°, 10.7°±0.2°, 12.7°±0.2°, 13.0°±0.2°, 13.9°±0.2°, 17.7°±0.2°, 18.6°±0.2°, 19.1°±0.2°, 21.5°±0.2°, 22.0°±0.2°, 22.5°±0.2°, 24.6°±0.2°, 25.3°±0.2°, and 25.7°±0.2° when irradiated with a Cu—Kα light source (XRPD5-3).

These peaks may be those having a relative intensity of about 20% or more.

The above crystalline form (ex. 5) may have an endothermic peak which has a starting point at about 115° C. and its lowest point at about 142° C., an exothermic peak at about 204° C., and an endothermic peak which has a starting point at about 210° C. and its lowest point at about 251° C., in a DSC (10° C./min).

The above crystalline form (ex. 5) may have a water content of about 3.5% (theoretical water content value of 3.33%) and a melting point of about 190° C. to 200° C.

The above crystalline form (ex. 5) shows a hygroscopicity measured at a very low level in the region with a relative humidity of 10% to 70% but the hygroscopicity in the region with a relative humidity of 70% or higher may be measured to be about 7%.

The above crystalline form (ex. 5) may have a $^{13}$C CP/MAS TOSS ssNMR spectrum comprising peaks at the following $^{13}$C chemical shifts: 42.5±0.2 ppm and 54.4±0.2 ppm (ssNMR5-1).

More specifically, the above crystalline form (ex. 5) may have a $^{13}$C CP/MAS TOSS ssNMR spectrum comprising peaks at the following $^{13}$C chemical shifts: 42.5±0.2 ppm, 45.4±0.2 ppm, 51.0±0.2 ppm and 54.4±0.2 ppm (ssNMR5-2).

The above crystalline form (ex. 5) may have a $^{13}$C CP/MAS TOSS ssNMR spectrum comprising peaks at the following $^{13}$C chemical shifts: 124.1±0.2 ppm and 131.8±0.2 ppm and 164.7±0.2 ppm (ssNMR5-3).

More specifically, the above crystalline form (ex. 5) may have a $^{13}$C CP/MAS TOSS ssNMR spectrum comprising peaks at the following $^{13}$C chemical shifts: 114.8±0.2 ppm, 124.1±0.2 ppm, 129.3±0.2 ppm, 131.8±0.2 ppm, 153.5±0.2 ppm and 164.7±0.2 ppm (ssNMR5-4).

More specifically, the above crystalline form (ex. 5) may have a $^{13}$C CP/MAS TOSS ssNMR spectrum comprising peaks at the following $^{13}$C chemical shifts: 42.5±0.2 ppm, 45.4±0.2 ppm, 51.0±0.2 ppm, 54.4±0.2 ppm, 114.8±0.2 ppm, 124.1±0.2 ppm, 129.3±0.2 ppm, 131.8±0.2 ppm, 153.5±0.2 ppm and 164.7±0.2 ppm (ssNMR5-5).

The above crystalline form (ex. 5) may have
(a) an X-ray powder diffraction (XRPD) pattern comprising peaks at diffraction angle 2θ values of 7.8°±0.2°, 22.5°±0.2° and 25.7°±0.2° when irradiated with a Cu—Kα light source; and
(b) a $^{13}$C solid state NMR spectrum comprising peaks at the following $^{13}$C chemical shifts: 42.5±0.2 ppm and 54.4±0.2 ppm.

The above crystalline form (ex. 5) may have
(a) an X-ray powder diffraction (XRPD) pattern comprising peaks at diffraction angle 2θ values of 7.8°±0.2°, 22.5°±0.2° and 25.7°±0.2° when irradiated with a Cu—Kα light source; and
(b) a $^{13}$C solid state NMR spectrum comprising peaks at the following $^{13}$C chemical shifts: 117.7±0.2 ppm, 153.1±0.2 ppm and 165.6±0.2 ppm.

The above crystalline form (ex. 5) may also be characterized by any other combination of lists of XRPD peaks (XRPD5-1 to XRPD5-3) and $^{13}$C chemical shifts (ssNMR5-1 to ssNMR5-5) as listed above.

In another exemplary embodiment (ex. 6), the present invention also provides a crystalline form (Type A) of a monohydrochloride hydrate, preferably dihydrate (1HCl.2H$_2$O), of the compound of Formula 1.

This crystalline form (ex. 6) exhibits an XRPD pattern comprising peaks at diffraction angles of 2θ=7.5°±0.2°, 15.1°±0.2° and 20.0°±0.2° when irradiated with a Cu—Kα light source (XRPD6-1).

More specifically, the above crystalline form (ex. 6) has an XRPD pattern comprising peaks at diffraction angles of 2θ=7.5°±0.2°, 15.1°±0.2°, 20.0°±0.2°, 21.2°±0.2°, and 25.1°±0.2° when irradiated with a Cu—Kα light source (XRPD6-2).

More specifically, the above crystalline form (ex. 6) has an XRPD pattern comprising peaks at diffraction angles of 2θ=6.8°±0.2°, 7.5°±0.2°, 15.1°±0.2°, 17.0°±0.2°, 18.1°±0.2°, 20.0°±0.2°, 21.2°±0.2°, 22.7°±0.2°, 23.0°±0.2°, 25.1°±0.2°, and 26.5°±0.2° when irradiated with a Cu—Kα light source (XRPD6-3).

These peaks may be those having a relative intensity of about 10% or more.

The above crystalline form (ex. 6) may have an endothermic peak which has a starting point at about 62° C. and its lowest point at about 90° C., and an endothermic peak which has a starting point at about 171° C. and its lowest point at about 182° C., in a DSC (10° C./min).

The above crystalline form (ex. 6) may have a water content of about 6.8% (theoretical water content value of 6.45%) and a melting point of about 190° C. to 200° C.

The hygroscopicity of the above crystalline form (ex. 6) in the region with a relative humidity of 10% to 90% may be measured to be about 2%, in a DVS.

The above crystalline form (ex. 6) may have a $^{13}$C CP/MAS TOSS ssNMR spectrum comprising peaks at the following $^{13}$C chemical shifts: 43.1±0.2 ppm and 53.2±0.2 ppm (ssNMR6-1).

More specifically, the above crystalline form (ex. 6) may have a $^{13}$C CP/MAS TOSS ssNMR spectrum comprising peaks at the following $^{13}$C chemical shifts: 43.1±0.2 ppm, 46.5±0.2 ppm, 48.1±0.2 ppm and 53.2±0.2 ppm (ssNMR6-2).

The above crystalline form (ex. 6) may have a $^{13}$C CP/MAS TOSS ssNMR spectrum comprising peaks at the following $^{13}$C chemical shifts: 117.6±0.2 ppm, 133.4±0.2 ppm and 164.3±0.2 ppm (ssNMR6-3).

More specifically, the above crystalline form (ex. 6) may have a $^{13}$C CP/MAS TOSS ssNMR spectrum comprising peaks at the following $^{13}$C chemical shifts: 117.6±0.2 ppm, 133.4±0.2 ppm, 137.8±0.2 ppm, 151.7±0.2 ppm, 164.3±0.2 ppm and 165.0±0.2 ppm (ssNMR6-4).

More specifically, the above crystalline form (ex. 6) may have a $^{13}$C CP/MAS TOSS ssNMR spectrum comprising peaks at the following $^{13}$C chemical shifts: 43.1±0.2 ppm, 46.5±0.2 ppm, 48.1±0.2 ppm, 53.2±0.2 ppm, 117.6±0.2 ppm, 133.4±0.2 ppm, 137.8±0.2 ppm, 151.7±0.2 ppm, 164.3±0.2 ppm and 165.0±0.2 ppm (ssNMR6-5).

The above crystalline form (ex. 6) may have
(a) an X-ray powder diffraction (XRPD) pattern comprising peaks at diffraction angle 2θ values of 7.5°±0.2°, 15.1°±0.2° and 20.0°±0.2° when irradiated with a Cu—Kα light source; and
(b) a $^{13}$C solid state NMR spectrum comprising peaks at the following $^{13}$C chemical shifts: 43.1±0.2 ppm and 53.2±0.2 ppm.

The above crystalline form (ex. 6) may have
(a) an X-ray powder diffraction (XRPD) pattern comprising peaks at diffraction angle 2θ values of 7.5°±0.2°, 15.1°±0.2° and 20.0°±0.2° when irradiated with a Cu—Kα light source; and
(b) a $^{13}$C solid state NMR spectrum comprising peaks at the following $^{13}$C chemical shifts: 117.6±0.2 ppm, 133.4±0.2 ppm and 164.3±0.2 ppm.

The above crystalline form (ex. 6) may also be characterized by any other combination of lists of XRPD peaks (XRPD6-1 to XRPD6-3) and $^{13}$C chemical shifts (ssNMR6-1 to ssNMR6-5) as listed above.

In another exemplary embodiment (ex. 7), the present invention provides a crystalline form (Type B) of a monohydrochloride hydrate, preferably dihydrate (1HCl.2H$_2$O), of the compound of Formula 1.

This crystalline form (ex. 7) exhibits an XRPD pattern comprising peaks at diffraction angles of 2θ=8.7°±0.2°, 19.4°±0.2° and 23.1°±0.2° when irradiated with a Cu—Kα light source (XRPD7-1).

More specifically, the above crystalline form (ex. 7) has an XRPD pattern comprising peaks at diffraction angles of 2θ=8.7°±0.2°, 11.6°±0.2°, 17.5°±0.2°, 19.4°±0.2° 23.1°±0.2°, and 26.1°±0.2° when irradiated with a Cu—Kα light source (XRPD7-2).

More specifically, the above crystalline form (ex. 7) has an XRPD pattern comprising peaks at diffraction angles of 2θ=8.7°±0.2°, 11.6°±0.2°, 14.4°±0.2°, 17.5°±0.2°, 19.4°±0.2°, 20.8°±0.2°, 21.9°±0.2°, 23.1°±0.2°, 26.1°±0.2° and 28.0°±0.2° when irradiated with a Cu—Kα light source.

These peaks may be those having a relative intensity of about 20% or more.

The above crystalline form (ex. 7) may have an endothermic peak which has a starting point at about 55° C. and its lowest point at about 71° C., and an endothermic peak which has a starting point at about 215° C. and its lowest point at about 222° C., in a DSC (10° C./min).

The above crystalline form (ex. 7) may have a water content of about 6.0% (theoretical water content value of 6.45%) and a melting point of about 190° C. to 200° C.

The hygroscopicity of the above crystalline form (ex. 7) in the region with a relative humidity of 10% to 90% may be measured to be about 14%, in a DVS.

The above crystalline form (ex. 7) may have a $^{13}$C CP/MAS TOSS ssNMR spectrum comprising peaks at the following $^{13}$C chemical shifts: 41.3±0.2 ppm, 48.8±0.2 ppm and 55.9±0.2 ppm (ssNMR7-1).

More specifically, the above crystalline form (ex. 7) may have a $^{13}$C CP/MAS TOSS ssNMR spectrum comprising peaks at the following $^{13}$C chemical shifts: 41.3±0.2 ppm, 42.6±0.2 ppm, 48.8±0.2 ppm, 50.0±0.2 ppm and 55.9±0.2 ppm (ssNMR7-2).

The above crystalline form (ex. 7) may have a $^{13}$C CP/MAS TOSS ssNMR spectrum comprising peaks at the following $^{13}$C chemical shifts: 119.0±0.2 ppm, 152.7±0.2 ppm and 165.0±0.2 ppm (ssNMR7-3).

More specifically, the above crystalline form (ex. 7) may have a $^{13}$C CP/MAS TOSS ssNMR spectrum comprising peaks at the following $^{13}$C chemical shifts: 119.0±0.2 ppm, 132.9±0.2 ppm, 139.0±0.2 ppm, 152.7±0.2 ppm, 163.5±0.2 ppm and 165.0±0.2 ppm (ssNMR7-4).

More specifically, the above crystalline form (ex. 7) may have a $^{13}$C CP/MAS TOSS ssNMR spectrum comprising peaks at the following $^{13}$C chemical shifts: 41.3±0.2 ppm, 42.6±0.2 ppm, 48.8±0.2 ppm, 50.0±0.2 ppm, 55.9±0.2 ppm, 119.0±0.2 ppm, 132.9±0.2 ppm, 139.0±0.2 ppm, 152.7±0.2 ppm, 163.5±0.2 ppm and 165.0±0.2 ppm (ssNMR7-5).

The above crystalline form (ex. 7) may have
(a) an X-ray powder diffraction (XRPD) pattern comprising peaks at diffraction angle 2θ values of 8.7°±0.2°, 19.4°±0.2° and 23.1°±0.2° when irradiated with a Cu—Kα light source; and
(b) a $^{13}$C solid state NMR spectrum comprising peaks at the following $^{13}$C chemical shifts: 41.3±0.2 ppm, 48.8±0.2 ppm and 55.9±0.2 ppm.

The above crystalline form (ex. 7) may have
(a) an X-ray powder diffraction (XRPD) pattern comprising peaks at diffraction angle 2θ values of 8.7°±0.2°, 19.4°±0.2° and 23.1°±0.2° when irradiated with a Cu—Kα light source; and
(b) a $^{13}$C solid state NMR spectrum comprising peaks at the following $^{13}$C chemical shifts: 119.0±0.2 ppm, 152.7±0.2 ppm and 165.0±0.2 ppm.

The above crystalline form (ex. 7) may also be characterized by any other combination of lists of XRPD peaks (XRPD7-1 to XRPD7-3) and $^{13}$C chemical shifts (ssNMR7-1 to ssNMR7-5) as listed above.

Medical Use and Pharmaceutical Composition

As disclosed in WO 2011/162515, the compound of Formula 1 has been shown to be useful for the selective and effective inhibitory activity against the growth of cancer cells induced by a mutation in epidermal growth factor receptor (EGFR) tyrosine kinase, and drug resistance thereof.

In one aspect the invention further provides a hydrochloride salt of the compound of Formula 1 or a crystalline form of hydrochloride salt of the compound of Formula 1 as described herein for use in the treatment of a cancer harboring one or more EGFR mutation.

In a further aspect the invention provides a method for the treatment of cancer comprising administering to a patient in need thereof a therapeutically effective amount of a hydrochloride salt of the compound of Formula 1 or a crystalline form of a hydrochloride salt of the compound of Formula 1 as described herein, wherein the cancer to be treated is a cancer harboring one or more EGFR mutation.

In a further aspect the cancer to be treated is a cancer harboring one or more EGFR mutations wherein at least one EGFR mutation is selected from Del19 (deletion in exon 19), L858R and T790M.

In a further aspect the cancer to be treated is a cancer harboring a Del19 EGFR mutation.

In a further aspect the cancer to be treated is a cancer harboring the EGFR mutation L858R.

In a further aspect the cancer to be treated is a cancer harboring the EGFR mutation T790M.

In a further aspect the cancer to be treated is a cancer harboring at least two EGFR mutations selected from the group consisting of Del19/T790M and L858R/T790M.

In this aspect, the hydrochloride salt of the compound of Formula 1 or a crystalline form of the hydrochloride salt of the compound of Formula 1 may be used for the preparation of a pharmaceutical composition for preventing or treating cancers or tumors induced by epidermal growth factor receptor tyrosine kinase or a mutant thereof. The pharmaceutical composition may be used to treat the same cancers harboring EGFR mutation as described for the hydrochloride or crystalline forms of the hydrochloride hereinbefore.

Accordingly, the present invention provides a pharmaceutical composition containing a hydrochloride salt of the compound of Formula 1, preferably in crystalline form, and at least one pharmaceutically acceptable carrier or diluent. The pharmaceutical composition may be used for the treatment of cancers or tumors induced by epidermal growth factor receptor tyrosine kinase or a mutant thereof.

The administration dose of the hydrochloride salt of the compound of Formula 1, preferably in crystalline form or a pharmaceutical composition containing the same may vary depending on the subject to be treated, severity of illness or health state of the subject, administration rate, physician's decision, etc., but it may be conventionally administered to a human subject having a body weight of e.g. 70 kg via an oral or parenteral administration route in an amount of from 10 mg to 2,000 mg as a free base based on the compound of Formula 1, preferably in an amount of 50 mg to 1,000 mg, 1 to 4 times daily or on an on/off schedule. In some cases, it may be more appropriate to administer a lower dosage than that mentioned above, a higher dosage than the above may be administered if it does not cause harmful side effects, and in the case when a significantly larger dosage is to be administered, the administration may be performed daily by several divided doses with a lesser dosage per administration.

The pharmaceutical composition according to the present invention may be prepared in various formulations for oral administration according to the conventional methods, e.g., tablets, pills, powders, capsules, syrups, emulsions, microemulsions, etc., or for parenteral administration, e.g., intramuscular, intravenous, or subcutaneous administrations.

The pharmaceutical composition may contain any conventional non-toxic, pharmaceutically acceptable carrier, diluent, adjuvant, excipient, or vehicle. When the pharmaceutical composition according to the present invention is prepared as a formulation for oral administration, the carrier to be used may include, e.g., cellulose, calcium silicate, corn starch, lactose, sucrose, dextrose, calcium phosphate, stearic acid, magnesium stearate, calcium stearate, gelatin, talc, surfactant, suspending agents, emulsifying agents, diluents, etc. Additionally, when the pharmaceutical composition is prepared as a formulation for oral administration, the diluents to be used may include lactose, mannitol, saccharide, microcrystalline cellulose, cellulose derivative, corn starch, etc. When the pharmaceutical composition according to the present invention is prepared as a formulation for injections, the carrier to be used may include, e.g., water, saline, an aqueous glucose solution, an aqueous sugar-like solution, alcohols, glycols (e.g., polyethylene glycol 400), ethers, oils, fatty acids, fatty acid esters, glycerides, surfactants, suspending agents, emulsifying agents, etc.

Hereinafter, the present invention will be described in more detail with reference to the following Examples. However, these Examples are for illustrative purposes only, and the invention is not intended to be limited by these Examples.

Analysis Apparatus and Method of Measurement

1. X-Ray Powder Diffraction (XRPD)

X-ray powder diffraction (XRPD) analyses of samples were performed in the range from 3° 2θ to 40° 2θ using a D8 Advance (Bruker ASX, Germany) analyzer. When the amount of a given sample was less than 100 mg, about 5 mg to 10 mg of the sample was gently compressed on a glass slide which was fit into a sample holder. When the amount of a given sample was greater than 100 mg, about 100 mg of the sample was gently compressed in a plastic sample holder so that the sample surface becomes flat and positioned immediately on top of the sample holder level.

The measurement was performed as follows:

Anode material (Kα): Cu Kα (1.54056 Å)
Scan range: 3° to 40°
Generator settings: 100 mA, 40.0 kV
Scan speed: 1 sec/step
Diver slit: 0.3°
Anti-scatter slit: 0.3°
Temperature: 20° C.
Step size: 0.02° 2θ
Rotation: use
Goniometer radius: 435 mm 2. Differential Scanning calorimeter (DSC)

Differential scanning calorimeter (DSC) analysis was performed in as STA-1000 (Scinco, Korea) at 30° C. to 350° C. A sample in an amount of 5 mg to 10 mg was weighed and added into an aluminum DSC fan, and the fan was sealed with a perforated aluminum lid in a non-sealing manner. Then, the sample was heated at a scan speed of 10° C./min from 30° C. to 350° C., and the heat flow reaction generated was monitored in a DSC.

3. Dynamic Vapor Sorption (DVS)

Dynamic vapor sorption (DVS) analysis was performed in a DVS advantage (Surface measurement system, United Kingdom) analyzer at 25° C. with a relative humidity of 0% to 90%.

A sample in an amount of 10 mg was placed into a wire-mesh vapor sorption balance pan and then attached to a DVS advantage dynamic vapor sorption balance via surface measurement systems. Until a stable weight was achieved (99.5% completion of steps), the sample was applied to a ramping profile with a relative humidity of 10% to 90% with a 10% increase of the sample while maintaining the sample in each step. Upon completion of the sorption cycle, the sample was dried using the same process while maintaining a relative humidity of below 0%. The changes in the sample weight during the adsorption/desorption cycle (repeated 3 times) were recorded and the hygroscopicity of the sample was measured.

4. Solid State Nuclear Magnetic Resonance Spectroscopy (ssNMR)

Solid State Nuclear Magnetic Resonance Spectroscopy (ssNMR) was performed for the purpose of comparing of the polymorphs by NMR spectroscopy in the solid state. A sample in an amount of 100 mg was weighed and added into a 4 mm sample tube. $^{13}$C NMR spectra ($^{13}$C CP/MAS TOSS ssNMR) were recorded at room temperature using a Bruker Avance II 500 MHz Solid NMR system (Bruker, Germany) analyzer with 4 mm probe type CP/MAS BB-1H under the following conditions:
  Frequency: 125.76 MHz,
  Spectral width: 20 kHz,
  Rotational speed of the sample at the magic angle: 5 kHz,
  Pulse Sequence: CP (Cross Polarization) SPINAL64 with decoupling (decoupling power of 80 kHz),
  Delay repeats; 5 s
  Contact time: 2 ms
  Number of scans: 4096.
  External standard: adamantane 5. High Performance Liquid Chromatography (HPLC)

High performance liquid chromatography (HPLC) analysis was performed for the purpose of analyzing purity and contents such as stability test, etc., using an Agilent 1100/1200 series HPLC Systems (Agilent, USA) analyzer, and the conditions used for HPLC are as follows.

Purity and Content Analysis Conditions: Thienopyrimidine Compound of Formula 1
  Column: Hydrosphere C18 (YMC), 5 μm (150 mm×4.6 mm)
  Column temperature: 30° C.
  Detector: UV spectrophotometer
  Detection wavelength: 254 nm
  Flow rate: 1.0 mL/min
  Time of analysis: 35 min
  Eluent: NaClO4-NaH2PO4—phosphate buffer solution (pH 2.5±0.1)/CH3CN=40/60 (v/v %)

6. Ion Chromatography (IC)

Ion chromatography (IC) analysis was performed for the purpose of analyzing the hydrochloric acid content in a hydrochloride salt using a Thermo Fisher Scientific ICS-2500 series IC Systems (Thermo Fisher Scientific, USA) analyzer, and the conditions used for IC analysis are as follows.

Conditions for Content Analysis: Thienopyrimidine Compound of Formula 1
  Column: IonPac AS19 (Dionex), (250 mm×4 mm), guard (50 mm×4 mm)
  Column temperature: 30° C.
  Detector: Conductivity detector (CD)
  Suppressor: ASRS 4 mm, current 40 mA
  Flow rate: 1.0 mL/min
  Time of analysis: 30 min
  Eluent: 10 mM KOH solution 7. Measurement of Water Content Water content was measured using a 795KFT Titrino (Metrohm, Switzerland) Karl Fischer titrator.

8. Measurement of Melting Point

Melting point was measured using an IA9200 (Electrothermal, UK) melting point measuring device.

EXAMPLES: PREPARATION OF A CRYSTALLINE FORM OF A HYDROCHLORIDE SALT OF A COMPOUND OF FORMULA 1

Example 1. Preparation of a Crystalline Form (Type A) of a Dihydrochloride Hydrate, Preferably Monohydrate (2HCl.1H2O), of a Compound of Formula 1

A compound of Formula 1 prepared according to the method disclosed in WO 2011/162515 referenced herein or a similar method thereof, as referenced herein, in an amount of 10.0 g was added into 100 mL of a 90% aqueous ethanol solution (ethanol/water=9/1). A concentrated HCl solution in an amount of 4 mL (45.2 mmol) was added thereto, stirred at room temperature for 6 hours, and the resulting precipitated solids were filtered. The resultant was washed with 20 mL of a 90% aqueous ethanol solution (ethanol/water=9/1) and dried to obtain 9.0 g of the title compound (yield: 80.0%).

Water content: 3.1% (theoretical value for a monohydrate: 3.11%)

Ion chromatography: 13.1% (theoretical value for a dihydrochloride: 13.0%)

In a further aspect the invention provides a crystalline form of a hydrochloride salt of the compound of Formula 1 prepared by a process comprising the steps of
  (a) adding an aqueous solution of an alcohol to the free base of the compound of Formula 1;
  (b) adding 1.5 to 3 eq. of HCl to the mixture obtained in step (a) (in relation to the free base); and
  (c) collecting the resulting precipitate.

Preferably, the free base used in this process is in amorphous form. Preferably the aqueous solution of an alcohol used in this process is an aqueous solution of ethanol or iso-propanol, more preferably the aqueous solution is a 85-95% aqueous solution of ethanol or iso-propanol, 90% is especially preferred. Most preferred is a 90% aqueous solution of ethanol. The preferred amount of HCl added is in the range of 2 to 2.5 eq. of HCl (in relation to the free base), most preferred is 2.2 to 2.3 eq. of HCl. Preferably, the mixture obtained after adding HCl is stirred a room temperature for 5 to 8 hours (6 hours are preferred). Collection of the precipitate can be achieved by filtration. Optionally, after collection the precipitate can be washed with the same aqueous solution of an alcohol as used in step (a) of the process.

Analysis of Characteristics

The results of XRPD, DSC, DVS and ssNMR analyses of the crystalline form prepared in Example 1 are shown in FIGS. 1A, 2A, 3A and 4A, respectively.

The peaks having a relative intensity (I/Io) of 3% or higher in the XRPD spectrum of the above crystalline form are shown in Table 1 below. When the peaks had I/Io ratios equal to or higher than 10%, they appeared at diffraction angles of 5.6°, 10.7°, 11.1°, 14.0°, 20.8°, 21.1°, 22.5°, and 27.3° (2θ±0.2°).

TABLE 1

| 2θ (±0.2) | d | I/I$_o$ (%) |
|---|---|---|
| 5.6 | 15.9 | 100 |
| 8.9 | 9.9 | 6.7 |
| 10.7 | 8.3 | 14.2 |
| 11.1 | 7.9 | 19.1 |
| 11.4 | 7.7 | 6.1 |
| 12.2 | 7.3 | 5.1 |
| 14.0 | 6.3 | 15.6 |
| 14.6 | 6.1 | 9.3 |
| 15.5 | 5.7 | 4.8 |
| 15.7 | 5.6 | 5.0 |
| 16.8 | 5.3 | 3.0 |
| 18.5 | 4.8 | 3.3 |
| 18.9 | 4.7 | 6.2 |
| 19.9 | 4.5 | 6.9 |
| 20.4 | 4.3 | 7.8 |
| 20.8 | 4.3 | 20.0 |
| 21.1 | 4.2 | 41.6 |
| 21.4 | 4.1 | 3.0 |
| 21.7 | 4.1 | 4.5 |

TABLE 1-continued

| 2θ (±0.2) | d | I/I$_o$ (%) |
|---|---|---|
| 22.5 | 4.0 | 10.2 |
| 23.2 | 3.8 | 9.0 |
| 24.1 | 3.7 | 6.5 |
| 24.7 | 3.6 | 3.6 |
| 25.0 | 3.6 | 8.8 |
| 26.4 | 3.4 | 6.5 |
| 26.8 | 3.3 | 4.5 |
| 27.3 | 3.3 | 24.7 |
| 27.7 | 3.2 | 3.6 |
| 28.8 | 3.1 | 6.5 |
| 29.4 | 3.0 | 6.5 |
| 29.8 | 3.0 | 5.0 |
| 30.1 | 3.0 | 4.4 |
| 30.6 | 2.9 | 3.0 |
| 31.3 | 2.9 | 4.0 |
| 32.4 | 2.8 | 4.4 |
| 34.7 | 2.6 | 3.5 |
| 37.9 | 2.4 | 3.3 |
| 39.7 | 2.3 | 3.0 |

2θ: diffraction angle,
d: distance between crystal faces,
I/I$_o$ (%): relative intensity (I indicates the intensity of each peak; I$_o$ indicates the intensity of the highest peak.)

In applying the conditions of measurement as disclosed herein the above crystalline form showed a broad endothermic peak between 25-150° C. associated with dehydration and an endotherm with a peak temperature about 238° C. which is associated with melting and decomposition.

The above crystalline form showed a water content of about 3.1% (theoretical water content value: 3.11%) in a Karl Fischer titrator and a melting point from about 202° C. to about 225° C.

In the DVS for the above crystalline form, the level of water absorption measured in the region with a relative humidity of 10% to 90% was very low (2-3%) and reversible. The above crystalline form was shown to be fully stable under a long-term storage condition (e.g., a temperature of 25° C. and a relative humidity of 60%), an accelerated condition (e.g., a temperature of 40° C. and a relative humidity of 75%), and a stress testing condition (e.g., a temperature of 60° C.).

In the ssNMR spectroscopy for the above crystalline form, the observed peaks were collected in the Table 2 below (expressed in ppm±0.2 ppm):

TABLE 2

| Peak # | Chemical Shift (ppm) |
|---|---|
| 1 | 44.6 |
| 2 | 45.4 |
| 3 | 50.8 |
| 4 | 56.6 |
| 5 | 108.4 |
| 6 | 112.5 |
| 7 | 114.4 |
| 8 | 116.5 |
| 9 | 119.1 |
| 10 | 120.8 |
| 11 | 128.1 |
| 12 | 130.7 |
| 13 | 134.8 |
| 14 | 140.4 |
| 15 | 144.2 |
| 16 | 146.8 |
| 17 | 149.6 |
| 18 | 152.6 |
| 19 | 164.3 |
| 20 | 165.9 |

Example 2. Preparation of a Crystalline Form (Type B) of a Dihydrochloride Hydrate, Preferably Monohydrate (2HCl.1H2O), of a Compound of Formula 1

The dihydrochloride hydrate, preferably trihydrate, (Type B) of a compound of Formula 1, prepared in Example 4 to be described later, in an amount of 1.0 g was dried in a chamber for stability testing at 60° C. for one week to obtain 1.0 g of the title compound.

Water content: 3.3% (theoretical value for a monohydrate: 3.1%)

Ion chromatography: 12.8% (theoretical value for a dihydrochloride: 13.0%)

Analysis of Characteristics

The result of XRPD analysis of the crystalline form prepared in Example 2 is shown in FIG. 1B.

The peaks having a relative intensity (I/Io) of 3% or higher in the XRPD spectrum of the above crystalline form are shown in Table 3 below. When the peaks had I/Io ratios equal to or higher than 10%, they appeared at diffraction angles of 6.4°, 8.1°, 9.7°, 12.8°, 13.7°, 14.3°, 16.0°, 19.0°, 20.8°, 21.2°, 22.0°, 24.1°, 24.6°, 24.9°, 26.0°, 26.3°, 26.8°, 27.1°, 28.1°, 29.2°, 30.9°, and 34.4° (2θ±0.2°).

TABLE 3

| 2θ (±0.2) | d | I/I$_o$ (%) |
|---|---|---|
| 3.2 | 27.3 | 7.9 |
| 3.4 | 26.1 | 6.6 |
| 6.4 | 13.9 | 59.6 |
| 7.3 | 12.0 | 3 |
| 8.1 | 10.8 | 46.9 |
| 9.7 | 9.1 | 31.3 |
| 10.2 | 8.6 | 3.2 |
| 10.9 | 8.1 | 4.4 |
| 12.8 | 6.9 | 50.6 |
| 13.3 | 6.6 | 8.4 |
| 13.7 | 6.4 | 10.4 |
| 14.3 | 6.2 | 13.6 |
| 14.7 | 6.0 | 8.7 |
| 15.3 | 5.8 | 8.1 |
| 16.0 | 5.5 | 31.8 |
| 16.4 | 5.4 | 8.9 |
| 16.8 | 5.3 | 8.7 |
| 18.3 | 4.8 | 8.7 |
| 18.7 | 4.7 | 8.5 |
| 19.0 | 4.7 | 18.5 |
| 19.6 | 4.5 | 8.8 |
| 20.8 | 4.3 | 100 |
| 21.2 | 4.2 | 15.2 |
| 21.6 | 4.1 | 8.5 |
| 22.0 | 4.0 | 78.3 |
| 23.4 | 3.8 | 5.7 |
| 24.1 | 3.7 | 42.6 |
| 24.6 | 3.6 | 17.2 |
| 24.9 | 3.6 | 14.2 |
| 25.4 | 3.5 | 6.2 |
| 25.6 | 3.5 | 9.3 |
| 26.0 | 3.4 | 15.7 |
| 26.3 | 3.4 | 32.4 |
| 26.8 | 3.3 | 22 |
| 27.1 | 3.3 | 35.3 |
| 28.1 | 3.2 | 24.5 |
| 28.6 | 3.1 | 5.5 |
| 29.2 | 3.1 | 16.3 |
| 30.9 | 2.9 | 10.1 |
| 32.2 | 2.8 | 9.9 |
| 32.7 | 2.7 | 7.0 |
| 33.3 | 2.7 | 5.1 |
| 33.9 | 2.6 | 4.4 |
| 34.4 | 2.6 | 13.5 |
| 35.4 | 2.5 | 7.3 |

TABLE 3-continued

| 2θ (±0.2) | d | I/I$_o$ (%) |
|---|---|---|
| 37.0 | 2.4 | 5.8 |
| 39.5 | 2.3 | 7.6 |

2θ: diffraction angle,
d: distance between crystal faces,
I/I$_o$ (%): relative intensity (I indicates the intensity of each peak; I$_o$ indicates the intensity of the highest peak.)

In the ssNMR spectroscopy for the above crystalline form, the observed peaks were collected in the Table 4 below (expressed in ppm±0.2 ppm):

TABLE 4

| Peak # | Chemical Shift (ppm) |
|---|---|
| 1 | 43.4 |
| 2 | 45.2 |
| 3 | 49.8 |
| 4 | 51.3 |
| 5 | 53.3 |
| 6 | 109.6 |
| 7 | 113.0 |
| 8 | 115.0 |
| 9 | 117.0 |
| 10 | 120.4 |
| 11 | 128.7 |
| 12 | 131.1 |
| 13 | 135.1 |
| 14 | 138.6 |
| 15 | 142.4 |
| 16 | 147.1 |
| 17 | 149.8 |
| 18 | 151.7 |
| 19 | 165.2 |
| — | — |
| — | — |

Example 3. Preparation of a Crystalline Form (Type A) of a Dihydrochloride Hydrate, Preferably Trihydrate (2HCl.3H2O), of a Compound of Formula 1

The dihydrochloride hydrate, preferably monohydrate, (Type A) of a compound of Formula 1 (Example 1) in an amount of 10.0 g was added into 100 mL of water. The mixture was heated under reflux, stirred for 30 minutes, cooled to room temperature, and stirred for 12 hours, and the resulting precipitated solids were filtered. The filtered precipitate was washed with 20 mL of water and dried to obtain 8.0 g of the title compound (yield: 80.0%).

Water content: 10.1% (theoretical value for a monohydrate: 8.8%)

Ion chromatography: 11.1% (theoretical value for a monohydrochloride: 13.0%)

Analysis of Characteristics

The results of XRPD, DSC, DVS and ssNMR analyses of the crystalline form prepared in Example 3 are shown in FIGS. 1C, 2B, 3B and 4B, respectively.

The peaks having a relative intensity (I/Io) of 3% or higher in the XRPD spectrum of the above crystalline form are shown in Table 5 below. When the peaks had I/Io ratios equal to or higher than 10%, they appeared at diffraction angles of 4.6°, 8.6°, 15.1°, 15.8°, 17.2°, 17.9°, 18.5°, 19.7°, 20.1°, 21.1°, 21.3°, 23.0°, 23.5°, 24.4°, 24.7°, 25.1°, 25.8°, 26.3°, 26.8°, 27.8°, and 28.4° (2θ±0.2°).

TABLE 5

| 2θ (±0.2) | d | I/I$_o$ (%) |
|---|---|---|
| 4.6 | 19.0 | 100 |
| 6.9 | 12.8 | 3.5 |
| 7.6 | 11.7 | 9.8 |
| 7.9 | 11.2 | 8.7 |
| 8.6 | 10.2 | 62.1 |
| 9.6 | 9.2 | 9.8 |
| 12.9 | 6.9 | 5.8 |
| 13.3 | 6.7 | 3.8 |
| 13.9 | 6.4 | 3.8 |
| 14.3 | 6.2 | 4.8 |
| 15.1 | 5.8 | 14.4 |
| 15.8 | 5.6 | 50.8 |
| 17.0 | 5.2 | 9.3 |
| 17.2 | 5.1 | 24.6 |
| 17.9 | 4.9 | 10.1 |
| 18.5 | 4.8 | 12.7 |
| 19.2 | 4.6 | 7.2 |
| 19.7 | 4.5 | 20.9 |
| 20.1 | 4.4 | 15.8 |
| 20.5 | 4.3 | 8.3 |
| 21.1 | 4.2 | 15.1 |
| 21.3 | 4.2 | 14.3 |
| 22.3 | 4.0 | 5.8 |
| 23.0 | 3.9 | 14.9 |
| 23.5 | 3.8 | 16.9 |
| 24.4 | 3.6 | 12.2 |
| 24.7 | 3.6 | 11.3 |
| 25.1 | 3.5 | 26.1 |
| 25.8 | 3.4 | 12.5 |
| 26.3 | 3.4 | 33.2 |
| 26.8 | 3.3 | 13.2 |
| 27.8 | 3.2 | 13.2 |
| 28.4 | 3.1 | 11.8 |
| 28.9 | 3.1 | 8.0 |
| 30.4 | 2.9 | 9.4 |
| 31.1 | 2.9 | 4.3 |
| 31.7 | 2.8 | 7.0 |
| 32.7 | 2.7 | 7.6 |
| 33.8 | 2.7 | 4.7 |
| 34.5 | 2.6 | 6.5 |
| 37.1 | 2.4 | 6.9 |
| 38.1 | 2.4 | 6.1 |

2θ: diffraction angle,
d: distance between crystal faces,
I/I$_o$ (%): relative intensity (I indicates the intensity of each peak; I$_o$ indicates the intensity of the highest peak.)

In applying the conditions of measurement as disclosed herein the above crystalline form showed endothermic peaks at about 51° C., about 95° C., and about 178° C., and an endothermic peak at about 218° C. in a DSC (10° C./min). In the DSC, the endothermic peaks at about 51° C., about 95° C., and about 178° C. indicate the dehydration point of the crystalline form of the dihydrochloride trihydrate, and the endothermic peak at about 218° C. indicates a melting point.

The above crystalline form showed a water content of about 10.1% (theoretical water content value: 8.8%) in a Karl Fischer titrator and a melting point from about 205° C. to about 210° C.

In the DVS for the above crystalline form, the level of water absorption in the region with a relative humidity of 10% to 40% was measured at a very low level, however, the level of water absorption in the region with a relative humidity of 40% or higher was measured at a higher level of about 9%. The above crystalline form was expected to maintain the crystalline form of the trihydrate due to absorption of water under a long-term storage condition (e.g., a temperature of 25° C. and a relative humidity of 60%) and an accelerated condition (e.g., a temperature of 40° C. and a relative humidity of 75%).

In the ssNMR spectroscopy for the above crystalline form, the observed peaks were collected in the Table 6 below (expressed in ppm±0.2 ppm):

TABLE 6

| Peak # | Chemical Shift (ppm) |
|---|---|
| 1 | 42.7 |
| 2 | 45.0 |
| 3 | 53.8 |
| 4 | 109.1 |
| 5 | 110.8 |
| 6 | 116.4 |
| 7 | 117.6 |
| 8 | 125.7 |
| 9 | 131.4 |
| 10 | 132.4 |
| 11 | 139.0 |
| 12 | 141.3 |
| 13 | 145.3 |
| 14 | 149.3 |
| 15 | 150.2 |
| 16 | 152.0 |
| 17 | 155.8 |
| 18 | 161.2 |
| 19 | 163.9 |
| 20 | 164.9 |
| 21 | 167.6 |

Example 4. Preparation of a Crystalline Form (Type B) of a Dihydrochloride Hydrate, Preferably Trihydrate (2HCl.3H2O), of a Compound of Formula 1

A dihydrochloride hydrate, preferably monohydrate, (Type A) of a compound of Formula 1 (Example 1) in an amount of 10.0 g was added into 100 mL of a 70% aqueous ethanol solution (ethanol/water=9/1). The mixture was heated under reflux, stirred for 30 minutes, cooled to room temperature, and stirred for 12 hours, and the resulting precipitated solids were filtered. The filtered precipitate was washed with 20 mL of the same solvent and dried to obtain 7.0 g of the title compound (yield: 70.0%).

Water content: 8.9% (theoretical value for a trihydrate: 8.8%)

Ion chromatography: 13.0% (theoretical value for a dihydrochloride: 13.0%)

Analysis of Characteristics

The results of XRPD, DSC, DVS and ssNMR analyses of the crystalline form prepared in Example 4 are shown in FIGS. 1D, 2C, 3C and 4C, respectively.

The peaks having a relative intensity (I/Io) of 3% or higher in the XRPD spectrum of the above crystalline form are shown in Table 7 below. When the peaks had I/Io ratios equal to or higher than 10%, they appeared at diffraction angles of 6.4°, 7.0°, 8.8°, 12.8°, 13.2°, 14.1°, 15.5°, 16.4°, 18.0°, 18.2°, 19.4°, 20.5°, 21.0°, 21.9°, 23.0°, 23.2°, 24.5°, 25.3°, 25.8°, 26.1°, 26.5°, 27.9°, 28.5°, 30.1°, 30.5°, and 31.0° (2θ±0.2°).

TABLE 7

| 2θ (±0.2) | d | I/I$_o$ (%) |
|---|---|---|
| 6.4 | 13.8 | 100 |
| 7.0 | 12.6 | 89.0 |
| 8.8 | 10.0 | 13.8 |
| 12.2 | 7.2 | 6.8 |
| 12.8 | 6.9 | 62 |
| 13.2 | 6.7 | 22.4 |
| 13.7 | 6.5 | 8.6 |
| 14.1 | 6.3 | 20.9 |
| 14.6 | 6.1 | 6.4 |
| 15.2 | 5.8 | 6.4 |
| 15.5 | 5.7 | 29.3 |
| 16.4 | 5.4 | 16.2 |
| 17.2 | 5.1 | 9.9 |
| 17.6 | 5.0 | 8.3 |
| 18.0 | 4.9 | 15.6 |
| 18.2 | 4.9 | 27.8 |
| 19.4 | 4.6 | 24.7 |
| 20.5 | 4.3 | 22.0 |
| 21.0 | 4.2 | 74.6 |
| 21.9 | 4.0 | 13.5 |
| 22.1 | 4.0 | 9.4 |
| 23.0 | 3.9 | 20.8 |
| 23.2 | 3.8 | 18.2 |
| 24.5 | 3.6 | 22.2 |
| 25.3 | 3.5 | 14.1 |
| 25.8 | 3.5 | 21.1 |
| 26.1 | 3.4 | 13.7 |
| 26.5 | 3.4 | 15.1 |
| 27.9 | 3.2 | 58.2 |
| 28.5 | 3.1 | 17.9 |
| 29.0 | 3.1 | 7.0 |
| 29.6 | 3.0 | 6.2 |
| 30.1 | 3.0 | 15.9 |
| 30.5 | 2.9 | 11.3 |
| 31.0 | 2.9 | 14.3 |
| 32.5 | 2.8 | 8.4 |
| 33.3 | 2.7 | 8.1 |
| 35.0 | 2.6 | 4.9 |
| 35.5 | 2.5 | 6.4 |
| 36.1 | 2.5 | 9.1 |
| 37.4 | 2.4 | 8.8 |
| 39.8 | 2.3 | 5.2 |

2θ: diffraction angle,
d: distance between crystal faces,
I/I$_o$ (%): relative intensity (I indicates the intensity of each peak; I$_o$ indicates the intensity of the highest peak.)

In applying the conditions of measurement as disclosed herein the above crystalline form showed an endothermic peak which has a starting point at about 50° C. and its lowest point at about 73° C., an endothermic peak at about 189° C., and an endothermic peak at about 222° C., in a DSC (10° C./min). In the DSC, the endothermic peaks at about 73° C. and 189° C. indicate the dehydration point of the crystalline form of the dihydrochloride trihydrate, and the endothermic peak at about 222° C. indicates a melting point.

The above crystalline form showed a water content of about 8.9% (theoretical water content value: 8.8%) in a Karl Fischer titrator and a melting point from about 210° C. to about 215° C.

In the DVS for the above crystalline form, the level of water absorption in the region with a relative humidity of 10% to 30% was very high, however, that in the region with a relative humidity of 40% or higher was measured to be very weak. The above crystalline form was expected to maintain the crystalline form of the trihydrate due to absorption of water under a long-term storage condition (e.g., a temperature of 25° C. and a relative humidity of 60%) and an accelerated condition (e.g., a temperature of 40° C. and a relative humidity of 75%).

In the ssNMR spectroscopy for the above crystalline form, the observed peaks were collected in the Table 8 below (expressed in ppm±0.2 ppm):

TABLE 8

| Peak # | Chemical Shift (ppm) |
|---|---|
| 1 | 43.8 |
| 2 | 46.7 |
| 3 | 49.9 |

TABLE 8-continued

| Peak # | Chemical Shift (ppm) |
|---|---|
| 4 | 53.8 |
| 5 | 110.0 |
| 6 | 111.9 |
| 7 | 117.7 |
| 8 | 119.2 |
| 9 | 120.6 |
| 10 | 130.1 |
| 11 | 131.5 |
| 12 | 132.7 |
| 13 | 140.4 |
| 14 | 144.2 |
| 15 | 147.6 |
| 16 | 149.5 |
| 17 | 150.4 |
| 18 | 153.1 |
| 19 | 157.2 |
| 20 | 165.6 |
| 21 | 166.7 |

Example 5: Preparation of a Crystalline Form of a Monohydrochloride Hydrate, Preferably Monohydrate (1HCl.1H2O), of a Compound of Formula 1

A compound of Formula 1 prepared according to the method disclosed in WO 2011/162515 or a similar method thereof, as referenced herein, in an amount of 5.0 g (0.010 mol) was added into a mixed solvent containing 15 mL of water and 35 mL of ethanol. The reaction mixture was treated with 0.97 mL (0.011 mol) of HCl dropwise and stirred at room temperature for 12 hours, and the resulting precipitated solids were filtered. The filtered precipitate was washed with a mixed solvent containing 1.5 mL of water and 3.5 mL of ethanol and dried at 50° C. to obtain 2.6 g of the title compound (yield: 48.0%).

Water content: 3.5% (theoretical value for a monohydrate: 3.33%)

Ion chromatography: 6.7% (theoretical value for a monohydrochloride: 7.0%)

Analysis of Characteristics

The results of XRPD, DSC, DVS and ssNMR analyses of the crystalline form prepared in Example 5 are shown in FIGS. 1E, 2D, 3D and 4D, respectively.

The peaks having a relative intensity (I/Io) of 3% or higher in the XRPD spectrum of the above crystalline form are shown in Table 9 below. When the peaks had I/Io ratios equal to or higher than 10%, they appeared at diffraction angles of 7.8°, 10.7°, 12.7°, 13.0°, 13.9°, 14.2°, 15.6°, 17.0°, 17.7°, 18.6°, 19.1°, 19.5°, 21.5°, 22.0°, 22.5°, 24.6°, 25.3°, 25.7°, 26.0°, 26.4°, 27.7°, 28.2°, 29.5°, and 34.8° (2θ±0.2°).

TABLE 9

| 2θ (±0.2) | d | I/I$_o$ (%) |
|---|---|---|
| 7.8 | 11.3 | 90.3 |
| 10.7 | 8.2 | 35.6 |
| 12.7 | 7.0 | 23.1 |
| 13.0 | 6.8 | 39.6 |
| 13.6 | 6.5 | 3.9 |
| 13.9 | 6.4 | 25.5 |
| 14.2 | 6.2 | 19.1 |
| 15.1 | 5.9 | 4.2 |
| 15.6 | 5.7 | 11.8 |
| 17.0 | 5.2 | 11.3 |
| 17.7 | 5.0 | 21.5 |
| 18.6 | 4.8 | 29.8 |
| 19.1 | 4.6 | 47.1 |

TABLE 9-continued

| 2θ (±0.2) | d | I/I$_o$ (%) |
|---|---|---|
| 19.5 | 4.6 | 10.6 |
| 20.0 | 4.4 | 9.5 |
| 21.5 | 4.1 | 20.6 |
| 22.0 | 4.0 | 35.6 |
| 22.5 | 4.0 | 68 |
| 23.4 | 3.8 | 8.1 |
| 24.6 | 3.6 | 32.7 |
| 25.3 | 3.5 | 33 |
| 25.7 | 3.5 | 100 |
| 26.0 | 3.4 | 17.9 |
| 26.4 | 3.4 | 17.1 |
| 27.4 | 3.3 | 8.2 |
| 27.7 | 3.2 | 15.6 |
| 28.2 | 3.2 | 18.5 |
| 29.0 | 3.1 | 6.6 |
| 29.5 | 3.0 | 11.3 |
| 30.0 | 3.0 | 5.5 |
| 30.7 | 2.9 | 8.6 |
| 31.5 | 2.8 | 7.5 |
| 32.9 | 2.7 | 5.1 |
| 33.4 | 2.7 | 5.4 |
| 34.0 | 2.6 | 7.5 |
| 34.8 | 2.6 | 10.1 |
| 35.5 | 2.5 | 9.0 |
| 36.9 | 2.4 | 3.5 |
| 37.6 | 2.4 | 6.1 |
| 37.9 | 2.4 | 7.3 |
| 38.7 | 2.3 | 5.5 |
| 39.3 | 2.3 | 4.6 |

2θ: diffraction angle,
d: distance between crystal faces,
I/I$_o$ (%): relative intensity (I indicates the intensity of each peak; I$_o$ indicates the intensity of the highest peak.)

In applying the conditions of measurement as disclosed herein the above crystalline form showed an endothermic peak which has a starting point at about 115° C. and its lowest point at about 142° C., an exothermic peak at about 204° C., and an endothermic peak which has a starting point at about 210° C. and its lowest point at about 251° C., in a DSC (10° C./min). In the DSC, the endothermic peak at about 142° C. indicates the dehydration point of the crystalline form of the monohydrochloride monohydrate, and the exothermic peak at about 204° C. indicates the occurrence of a partial phase transition, and an endothermic peak at about 251° C. indicates a melting point.

The above crystalline form showed a water content of about 3.5% (theoretical water content value of a monohydrate: 3.33%) in a Karl Fischer titrator and a melting point from about 190° C. to about 200° C.

In the DVS for the above crystalline form, the level of water absorption in the region with a relative humidity of 10% to 70% was very low, however, that in the region with a relative humidity of 70% or higher was measured to be about 7%. From these results, the above crystalline form was expected to be stable under a long-term storage condition (e.g., a temperature of 25° C. and a relative humidity of 60%), and stable under an accelerated condition (e.g., a temperature of 40° C. and a relative humidity of 75%) due to absorption of water.

In the ssNMR spectroscopy for the above crystalline form, the observed peaks were collected in Table 10 (expressed in ppm±0.2 ppm):

TABLE 10

| Peak # | Chemical Shift (ppm) |
|---|---|
| 1 | 42.5 |
| 2 | 45.4 |

TABLE 10-continued

| Peak # | Chemical Shift (ppm) |
|---|---|
| 3 | 51.0 |
| 4 | 54.4 |
| 5 | 107.0 |
| 6 | 112.4 |
| 7 | 114.8 |
| 8 | 116.9 |
| 9 | 120.1 |
| 10 | 122.9 |
| 11 | 124.1 |
| 12 | 129.3 |
| 13 | 131.8 |
| 11 | 138.5 |
| 15 | 142.1 |
| 16 | 146.3 |
| 17 | 153.5 |
| 18 | 159.2 |
| 19 | 164.7 |
| — | — |
| — | — |

Example 6. Preparation of a Crystalline Form (Type A) of a Monohydrochloride Hydrate, Preferably Dihydrate (1HCl.2H2O), of a Compound of Formula 1

A dihydrochloride hydrate, preferably monohydrate, (Type A) of the compound of Formula 1 prepared in Example 1 in an amount of 30.0 g was added to 900 mL of water. The mixture was stirred at room temperature for 72 hours, and the resulting precipitated solids were filtered. The filtered precipitate was washed with 60 mL of the same solvent and dried to obtain 20 g of the title compound (yield: 67.0%).

Water content: 6.8% (theoretical value for a dihydrate: 6.45%)

Ion chromatography: 6.9% (theoretical value for a monohydrochloride: 7.0%)

Analysis of Characteristics

The results of XRPD, DSC, DVS and ssNMR analyses of the crystalline form prepared in Example 6 are shown in FIGS. 1F, 2E, 3E and 4E, respectively.

The peaks having a relative intensity (I/Io) of 3% or higher in the XRPD spectrum of the above crystalline form are shown in Table 11 below. When the peaks had I/Io ratios equal to or higher than 10%, they appeared at diffraction angles of 6.8°, 7.5°, 15.1°, 17.0°, 18.1°, 20.0°, 21.2°, 22.7°, 23.0°, 25.1°, and 26.5° (2θ±0.2°).

TABLE 11

| 2θ (±0.2) | d | I/I$_o$ (%) |
|---|---|---|
| 6.8 | 12.9 | 12.5 |
| 7.5 | 11.8 | 100 |
| 12.4 | 7.1 | 9.7 |
| 13.2 | 6.7 | 2.9 |
| 15.1 | 5.9 | 54.1 |
| 17.0 | 5.2 | 10.4 |
| 18.1 | 4.9 | 12.5 |
| 20.0 | 4.4 | 39.4 |
| 20.7 | 4.3 | 6.6 |
| 21.2 | 4.2 | 16.1 |
| 21.9 | 4.1 | 5.6 |
| 22.7 | 3.9 | 12.4 |
| 23.0 | 3.9 | 10 |
| 23.9 | 3.7 | 3.6 |
| 24.2 | 3.7 | 3.2 |
| 25.1 | 3.5 | 20.1 |
| 25.4 | 3.5 | 6.1 |
| 26.5 | 3.4 | 14.3 |
| 27.3 | 3.3 | 2.9 |
| 28.6 | 3.1 | 3.8 |
| 29.6 | 3.0 | 5.0 |
| 30.5 | 2.9 | 5.6 |
| 31.3 | 2.9 | 6.1 |
| 33.7 | 2.7 | 2.5 |

2θ: diffraction angle, d: distance between crystal faces,
I/I$_o$ (%): relative intensity (I indicates the intensity of each peak; I$_o$ indicates the intensity of the highest peak.)

In applying the conditions of measurement as disclosed herein the above crystalline form showed an endothermic peak which has a starting point at about 62° C. and its lowest point at about 90° C., and an endothermic peak which has a starting point at about 171° C. and its lowest point at about 182° C., in a DSC (10° C./min). In the DSC, the endothermic peak at about 90° C. indicates the dehydration point of the crystalline form of the monohydrochloride dihydrate, and an endothermic peak at about 182° C. indicates a melting point.

The above crystalline form showed a water content of about 6.8% (theoretical water content value: 6.45%) in a Karl Fischer titrator and a melting point from about 190° C. to about 200° C.

In the DVS for the above crystalline form, the level of water absorption in the region with a relative humidity of 10% to 90% was measured to be as low as about 2%. The above crystalline form was expected to be stable under a long-term storage condition (e.g., a temperature of 25° C. and a relative humidity of 60%) and an accelerated condition (e.g., a temperature of 40° C. and a relative humidity of 75%).

In the ssNMR spectroscopy for the above crystalline form, the observed peaks were collected in Table 12 below (expressed in ppm±0.2 ppm):

TABLE 12

| Peak # | Chemical Shift (ppm) |
|---|---|
| 1 | 43.1 |
| 2 | 46.5 |
| 3 | 48.1 |
| 4 | 53.2 |
| 5 | 107.5 |
| 6 | 115.9 |
| 7 | 117.6 |
| 8 | 122.4 |
| 9 | 123.1 |
| 10 | 127.6 |
| 11 | 130.0 |
| 12 | 133.4 |
| 13 | 137.8 |
| 14 | 146.0 |
| 15 | 151.7 |
| 16 | 157.6 |
| 17 | 164.3 |
| 18 | 165.0 |

Example 7. Preparation of a Crystalline Form (Type B) of a Monohydrochloride Hydrate, Preferably Dihydrate (1HCl.2H2O), of a Compound of Formula 1

The dihydrochloride hydrate, preferably monohydrate, of the compound of Formula 1 prepared in Example 1 in the amount of 15.0 g (0.026 mol) was added into a mixed solvent consisting of water (45 mL) and ethanol (105 mL).

To the reaction mixture was dropwise added with an aqueous solution, in which 2.18 g (0.055 mol) of sodium hydroxide was dissolved in 2.18 g (0.055 mol) of water, stirred at room temperature for 30 minutes, and dropwise added with 2.75 mL (0.031 mol) hydrochloric acid. The reaction mixture was stirred at room temperature for 12 hours, and the resulting precipitated solids were filtered. The filtered precipitate was washed with a mixed solvent consisting of water (4.5 mL) and ethanol (10.5 mL), and dried at 50° C. to obtain 8.5 g of the title compound (yield: 60.0%).

Water content: 6.0% (theoretical value for a dihydrate: 6.45%)

Ion chromatography: 7.2% (theoretical value for a monohydrochloride: 7.0%)

Analysis of Characteristics

The results of XRPD, DSC, DVS and ssNMR analyses of the crystalline form prepared in Example 7 are shown in FIGS. 1G, 2F, 3F and 4F, respectively.

The peaks having a relative intensity (I/Io) of 3% or higher in the XRPD spectrum of the above crystalline form are shown in Table 13 below. When the peaks had I/Io ratios equal to or higher than 10%, they appeared at diffraction angles of 8.7°, 11.6°, 13.1°, 13.3°, 14.4°, 15.3°, 17.5°, 18.1°, 18.6°, 19.4°, 20.1°, 20.8°, 21.9°, 23.1°, 24.2°, 26.1°, 26.6°, 27.2°, 28.0°, 30.5°, and 31.7° (2θ±0.2°).

TABLE 13

| 2θ (±0.2) | d | I/I$_o$(%) |
| --- | --- | --- |
| 7.9 | 11.3 | 3.3 |
| 8.7 | 10.2 | 100 |
| 10.4 | 8.5 | 3.0 |
| 11.6 | 7.7 | 29.6 |
| 13.1 | 6.8 | 16.4 |
| 13.3 | 6.7 | 18 |
| 14.4 | 6.1 | 21.5 |
| 15.0 | 5.9 | 4.8 |
| 15.3 | 5.8 | 11.8 |
| 16.6 | 5.3 | 3.4 |
| 17.5 | 5.1 | 33.5 |
| 18.1 | 4.9 | 12.0 |
| 18.6 | 4.8 | 13.8 |
| 19.4 | 4.6 | 98.8 |
| 20.1 | 4.4 | 13.6 |
| 20.8 | 4.3 | 23.8 |
| 21.9 | 4.1 | 24.1 |
| 23.1 | 3.8 | 48.5 |
| 24.2 | 3.7 | 12.5 |
| 24.6 | 3.6 | 9.7 |
| 25.3 | 3.5 | 6.0 |
| 26.1 | 3.4 | 30.8 |
| 26.6 | 3.3 | 15.5 |
| 27.2 | 3.3 | 13.1 |
| 28.0 | 3.2 | 20.4 |
| 28.8 | 3.1 | 6.4 |
| 29.9 | 3.0 | 4.8 |
| 30.5 | 2.9 | 11.5 |
| 30.9 | 2.9 | 7.2 |
| 31.7 | 2.8 | 14.3 |
| 32.4 | 2.8 | 7.2 |
| 33.2 | 2.7 | 3.1 |
| 35.2 | 2.5 | 4.2 |
| 35.6 | 2.5 | 5.3 |
| 36.7 | 2.4 | 6.9 |
| 37.7 | 2.4 | 3.9 |
| 39.4 | 2.3 | 3.0 |

2θ: diffraction angle,
d: distance between crystal faces,
I/I$_o$ (%): relative intensity (I indicates the intensity of each peak; I$_o$ indicates the intensity of the highest peak.)

In applying the conditions of measurement as disclosed herein the above crystalline form showed an endothermic peak which has a starting point at about 55° C. and its lowest point at about 71° C., and an endothermic peak which has a starting point at about 215° C. and its lowest point at about 222° C., in a DSC (10° C./min). In the DSC, the endothermic peak at about 71° C. indicates the dehydration point of the crystalline form of the monohydrochloride dihydrate, and an endothermic peak at about 222° C. indicates a melting point.

The above crystalline form showed a water content of about 6.0% (theoretical water content value: 6.45%) in a Karl Fischer titrator and a melting point from about 190° C. to about 200° C.

In the DVS for the above crystalline form, the level of water absorption in the region with a relative humidity of 10% to 70% was very low, but the level of water absorption in the region with a relative humidity of 70% or higher was measured to be about 14%. From these, the above crystalline form was expected to be stable under a long-term storage condition (e.g., a temperature of 25° C. and a relative humidity of 60%) and an accelerated condition (e.g., a temperature of 40° C. and a relative humidity of 75%).

In the ssNMR spectroscopy for the above crystalline form, the observed peaks were collected in Table 14 below (expressed in ppm±0.2 ppm):

TABLE 14

| Peak # | Chemical Shift (ppm) |
| --- | --- |
| 1 | 41.3 |
| 2 | 42.6 |
| 3 | 48.8 |
| 4 | 50.1 |
| 5 | 55.9 |
| 6 | 109.4 |
| 7 | 111.5 |
| 8 | 117.2 |
| 9 | 119.0 |
| 10 | 121.4 |
| 11 | 122.0 |
| 12 | 122.6 |
| 13 | 128.0 |
| 14 | 130.7 |
| 15 | 132.9 |
| 16 | 139.0 |
| 17 | 145.7 |
| 18 | 152.7 |
| 19 | 157.4 |
| 20 | 163.5 |
| 21 | 165.0 |

Comparative Example 1: Preparation of an Amorphous Form of a Dihydrochloride (2HCl) of a Compound of Formula 1

A dihydrochloride hydrate, preferably monohydrate, (Type A) of the compound of Formula 1 (Example 1) in an amount of 10 g was added to 200 mL of methanol. The mixture was stirred at 40° C. for 30 minutes, and the resulting insoluble solids were filtered. The filtered precipitate was distilled under reduced pressure to obtain 9.0 g of the title compound (yield: 90.0%).

Water content: 6.9%

Ion chromatography: 12.1% (theoretical value of a dihydrochloride: 13.0%)

Analysis of Characteristics

The results of XRPD, DSC, DVS and ssNMR analyses of the amorphous form prepared in Comparative Example 1 are shown in FIGS. 1H, 2G, 3G and 4G, respectively.

The amorphous form failed to show any particular diffraction pattern in an XRPD spectrum.

Additionally, the amorphous form failed to show any particular endothermic/exothermic curve in a DSC (10° C./min).

Additionally, the amorphous form showed a very high level of water absorption in the region with a relative humidity of 10% to 90% in a DVS. From these results, the above amorphous form was expected to be unstable under a long-term storage condition (e.g., a temperature of 25° C. and a relative humidity of 60%) and under an accelerated condition (e.g., a temperature of 40° C. and a relative humidity of 75%) due to absorption of water, and in fact, was shown to have a hygroscopicity of 13% to 15% under conditions of a temperature of 25° C. and a relative humidity of 60%; and a temperature of 40° C. and a relative humidity of 75%.

Additionally, the amorphous form showed a significant fluctuation in its water content, as measured by a Karl Fischer titrator, showing a water content of 4% to 8% (theoretical water content value: 8.81%). The melting point was not particularly specified and the decomposition at about 250° C. was observed.

In the ssNMR spectroscopy for the above amorphous form, the observed peaks were collected in the Table 15 below (expressed in ppm±0.2 ppm):

TABLE 15

| Peak # | Chemical Shift (ppm) |
| --- | --- |
| 1 | 44.5 |
| 2 | 49.8 |
| 3 | 53.5 |
| 4 | 117.7 |
| 5 | 130.2 |
| 6 | 140.9 |
| 7 | 151.1 |
| 8 | 164.8 |
| — | — |

Test Example 1: Test of Measurement of Water Solubility

In order to measure water solubility, each sample of the polymorphs of the hydrochloride salts of the compound of Formula 1, prepared in Examples 1 to 7, was prepared in non-ionic water under the conditions described below. Each of the solutions was analyzed by high performance liquid chromatography (HPLC) according to the conditions for measurement of contents of the compound of Formula 1, and the amount dissolved based on the amount of the compound of Formula 1 was measured (LOD: >0.001 mg/mL), and the values were calculated. The results are shown in Table 16 below.

Specifically, each sample of the polymorphs in an amount of 500 mg was added to 5 mL of water, blended at 20° C. to 25° C. using a Voltamixer, and filtered with a GH Polypro membrane Acrodisc, PALL (pore size: 0.2 μm). The filtrate was diluted with a diluent used for HPLC in a 1:100 ratio to obtain the samples.

TABLE 16

| Polymorph | Formula 1 (amorphous free base) | Example 1 | Example 3 | Example 4 | Example 5 | Example 6 |
| --- | --- | --- | --- | --- | --- | --- |
| Conc. of solution (mg/mL) | 100 | 100 | 100 | 100 | 100 | 100 |
| Solubility (mg/mL) | 0.0001 | 50.39 | 7.76 | 10.66 | 0.42 | 0.57 |
| pH of solution | 7.3 | 1.7 | 2.1 | 1.7 | 4.7 | 4.9 |

As shown in Table 16 above, the solubility of the hydrochloride salt of the compound of Formula 1 was significantly higher than that of the compound (free base) of Formula 1. In particular, the solubility of the crystalline form of the dihydrochloride salt of the compound of Formula 1 was significantly higher than that of the monohydrochloride, and the crystalline form of Example 1 showed the highest water solubility among the crystalline polymorphs of the dihydrochloride salt.

Accordingly, considering the conditions such as elution, etc., the crystalline form of Example 1 (the dihydrochloride hydrate, preferably monohydrate, (Type A) of the compound of Formula 1) is expected to be most advantageous from the aspect of a pharmaceutical composition.

The invention claimed is:

1. A crystalline form of a dihydrochloride monohydrate (2HCl.1H$_2$O) of the compound of Formula 1, wherein the crystalline form has an X-ray powder diffraction (XRPD) pattern comprising peaks at diffraction angle 2θ values of 5.6°±0.2°, 11.1°±0.2°, 14.0°±0.2°, 20.8°±0.2, and 27.3°±0.2° when irradiated with a Cu—Kα light source:

Formula 1

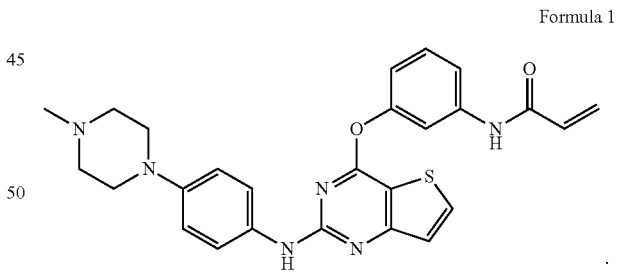

2. The crystalline form of the dihydrochloride monohydrate of claim 1, wherein the crystalline form further comprises peaks at diffraction angle 2θ value of 21.1°±0.2° when irradiated with a Cu—Kα light source.

3. The crystalline form of the dihydrochloride monohydrate of claim 1, wherein the crystalline form has a $^3$C solid state NMR spectrum comprising peaks at the following $^{13}$C chemical shifts: 44.6±0.2 ppm and 56.6±0.2 ppm.

4. The crystalline form of the dihydrochloride monohydrate of claim 1, wherein the crystalline form has a $^{13}$C solid state NMR spectrum comprising peaks at the following $^{13}$C chemical shifts: 149.6±0.2 ppm, 152.6±0.2 ppm and 164.3±0.2 ppm.

5. The crystalline form of the dihydrochloride monohydrate of claim 2, wherein the crystalline form has
a $^{13}C$ solid state NMR spectrum comprising peaks at the following $^{13}C$ chemical shifts: 44.6±0.2 ppm and 56.6±0.2 ppm.

6. The crystalline form of the dihydrochloride monohydrate of claim 2, wherein the crystalline form has a $^{13}C$ solid state NMR spectrum comprising peaks at the following $^{13}C$ chemical shifts: 149.6±0.2 ppm, 152.6±0.2 ppm and 164.3±0.2 ppm.

7. A crystalline form of a dihydrochloride monohydrate (2HCl.1H$_2$O) of the compound of Formula 1 having an X-ray powder diffraction pattern comprising peaks at diffraction angle 2θ values of 6.4°±0.2°, 8.1°±0.2°, 9.7°±0.2°, 12.8°±0.2°, 16.0°±0.2°, 20.8°±0.2°±22.0°±0.2°, 24.1°±0.2°, 26.3°±0.2°, and 27.1°±0.2 when irradiated with a Cu—Kα light source:

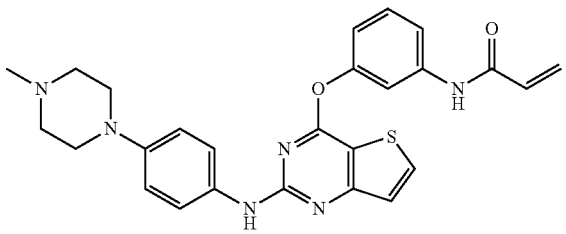

Formula 1

8. The crystalline form of the dihydrochloride monohydrate of claim 7, wherein the crystalline form has a $^{13}C$ solid state NMR spectrum comprising peaks at the following $^{13}C$ chemical shifts: 43.4±0.2 ppm and 45.2±0.2 ppm.

9. The crystalline form of the dihydrochloride monohydrate of claim 7, wherein the crystalline form has a $^3C$ solid state NMR spectrum comprising peaks at the following $^{13}C$ chemical shifts: 117.0±0.2 ppm, 149.8±0.2 ppm and 165.2±0.2 ppm.

10. A crystalline form of a dihydrochloride trihydrate (2HCl.3H$_2$O) of the compound of Formula 1 having an X-ray powder diffraction pattern comprising peaks at diffraction angle 2θ values of 4.6°±0.2°, 8.6°±0.2°, 15.8°±0.2°, 17.2°±0.2°, 19.7°±0.2°, 25.1°±0.2°, and 26.3°±0.2° when irradiated with a Cu—Kα light source:

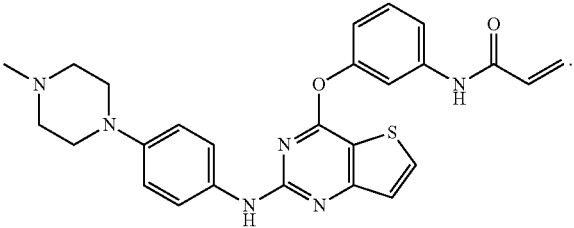

Formula 1

11. The crystalline form of the dihydrochloride trihydrate of claim 10, wherein the crystalline form has a $^{13}C$ solid state NMR spectrum comprising peaks at the following $^{13}C$ chemical shifts: 45.0±0.2 ppm and 53.8±0.2 ppm.

12. The crystalline form of the dihydrochloride trihydrate of claim 10, wherein the crystalline form has a $^{13}C$ solid state NMR spectrum comprising peaks at the following $^{13}C$ chemical shifts: 117.6±0.2 ppm and 150.2±0.2 ppm.

13. A crystalline form of a dihydrochloride trihydrate (2HCl.3H$_2$O) of the compound of Formula 1 having an X-ray powder diffraction pattern comprising peaks at diffraction angle 2θ values of 6.4°±0.2°, 7.0°±0.2°, 12.8°±0.2°, 15.5°±0.2°, 18.2°±0.2°, 21.0°±0.2°, and 27.9°±0.2 when irradiated with a Cu—Kα light source:

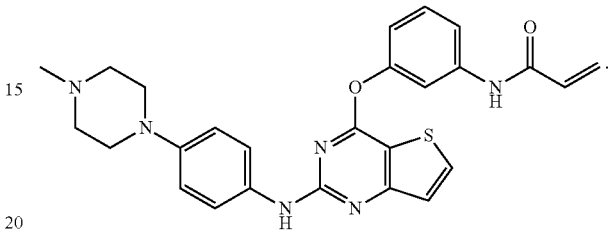

Formula 1

14. The crystalline form of the dihydrochloride trihydrate of claim 13, wherein the crystalline form has a $^{13}C$ solid state NMR spectrum comprising peaks at the following $^{13}C$ chemical shifts: 43.8±0.2 ppm and 53.8±0.2 ppm.

15. The crystalline form of the dihydrochloride trihydrate of claim 13, wherein the crystalline form has a $^{13}C$ solid state NMR spectrum comprising peaks at the following $^{13}C$ chemical shifts: 117.7±0.2 ppm, 153.1±0.2 ppm and 165.6±0.2 ppm.

16. A crystalline form of a monohydrochloride monohydrate (1HCl.1H$_2$O) of the compound of Formula 1 having an X-ray powder diffraction pattern comprising peaks at diffraction angle 2θ values of 7.8°±0.2°, 10.7°±0.2°, 13.0°±0.2°, 18.6°±0.2°, 19.1°±0.2°, 22.0°±0.2°, 22.5°±0.2°, 24.6°±0.2° and 25.3°±0.2, and 25.7°±0.2° when irradiated with a Cu—Kα light source:

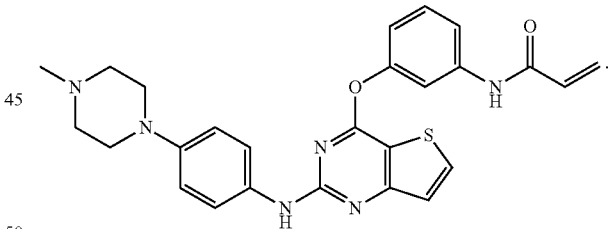

Formula 1

17. The crystalline form of the monohydrochloride monohydrate of claim 16, wherein the crystalline form has having a $^3C$ solid state NMR spectrum comprising peaks at the following $^3C$ chemical shifts: 42.5±0.2 ppm and 54.4±0.2 ppm.

18. The crystalline form of the monohydrochloride monohydrate of claim 16, wherein the crystalline form has a $^{13}C$ solid state NMR spectrum comprising peaks at the following $^{13}C$ chemical shifts: 124.1±0.2 ppm, 131.8±0.2 ppm and 164.7±0.2 ppm.

19. A crystalline form of a monohydrochloride dihydrate (1HCl.2H$_2$O), of the compound of Formula 1 having an X-ray powder diffraction pattern comprising peaks at diffraction angle 2θ values of 7.5°±0.2°, 15.1°±0.2°, 20.0°±0.2°, 21.2°±0.2° and 25.1°±0.2° when irradiated with a Cu—Kα light source:

Formula 1

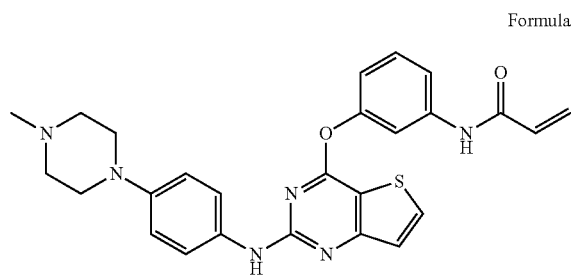

Formula 1

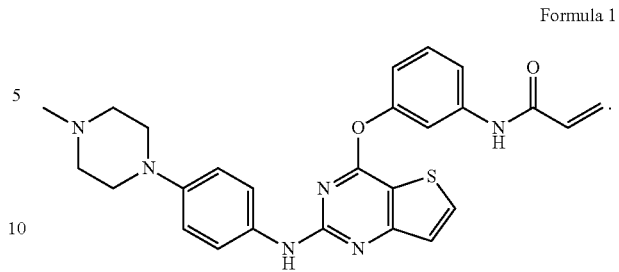

20. The crystalline form of the monohydrochloride dihydrate of claim 19, wherein the crystalline form has a $^{13}$C solid state NMR spectrum comprising peaks at the following $^{13}$C chemical shifts: 43.1±0.2 ppm and 53.2±0.2 ppm.

21. The crystalline form of the monohydrochloride dihydrate of claim 19, wherein the crystalline form has a $^{13}$C solid state NMR spectrum comprising peaks at the following $^{13}$C chemical shifts: 117.6±0.2 ppm, 133.4±0.2 ppm and 164.3±0.2 ppm.

22. A crystalline form of a monohydrochloride dihydrate (1HCl.2H$_2$O), of the compound of Formula 1 having an X-ray powder diffraction pattern comprising peaks at diffraction angle 2θ values of 8.7°±0.2°, 11.6°±0.2°, 17.5°±0.2°, 19.4°±0.2°, 23.1°±0.2°, and 26.1°±0.2° when irradiated with a Cu—Kα light source:

23. The crystalline form of the monohydrochloride dihydrate of claim 22, wherein the crystalline form has a $^{13}$C solid state NMR spectrum comprising peaks at the following $^{13}$C chemical shifts: 41.3±0.2 ppm, 48.8±0.2 ppm and 55.9±0.2 ppm.

24. The crystalline form of the monohydrochloride dihydrate of claim 22, wherein the crystalline form has a $^{13}$C solid state NMR spectrum comprising peaks at the following $^{13}$C chemical shifts: 119.0±0.2 ppm, 152.7±0.2 ppm and 165.0±0.2 ppm.

25. The crystalline form of the dihydrochloride monohydrate of claim 1, wherein the crystalline form is substantially pure.

26. A pharmaceutical composition comprising the dihydrochloride monohydrate of claim 1 and at least one pharmaceutically acceptable carrier or diluent.

* * * * *